US006763993B2

(12) United States Patent
Bolduc et al.

(10) Patent No.: US 6,763,993 B2
(45) Date of Patent: Jul. 20, 2004

(54) SURGICAL STAPLING INSTRUMENT AND METHOD THEREOF

(76) Inventors: Lee R. Bolduc, 761-1/2 Palo Alto Ave., Mountain View, CA (US) 94041; Christopher F. Heck, 1956 Coventry Rd., Columbus, OH (US) 43212

(*) Notice: Subject to any disclaimer, the term of this patent is extended or adjusted under 35 U.S.C. 154(b) by 0 days.

(21) Appl. No.: 10/441,447

(22) Filed: May 20, 2003

(65) Prior Publication Data

US 2003/0201301 A1 Oct. 30, 2003

Related U.S. Application Data

(63) Continuation of application No. 09/776,612, filed on Feb. 2, 2001, now Pat. No. 6,588,643, which is a continuation of application No. 09/391,297, filed on Sep. 7, 1999, now Pat. No. 6,209,773, which is a continuation of application No. 09/045,673, filed on Mar. 20, 1998, now Pat. No. 5,947,363, which is a continuation of application No. 08/597,691, filed on Feb. 6, 1996, now Pat. No. 5,732,872, which is a continuation-in-part of application No. 08/550,285, filed on Oct. 31, 1995, now Pat. No. 5,709,335, which is a continuation of application No. 08/261,167, filed on Jun. 17, 1994, now abandoned.

(51) Int. Cl.[7] .............................................. A61B 17/068
(52) U.S. Cl. ................... 227/176.1; 227/19; 227/179.1; 606/219
(58) Field of Search ................................ 227/19, 175.1, 227/176.1, 179.1; 606/194, 219

(56) References Cited

U.S. PATENT DOCUMENTS

| 1,251,258 A | 12/1917 | Magil |
| 1,759,670 A | 4/1930 | Treat |
| 1,918,890 A | 7/1933 | Bacon |
| 1,967,056 A | 7/1934 | Horton |
| 2,434,030 A | 1/1948 | Yeomans |
| 2,638,901 A | 5/1953 | Sugarbaker |
| 2,707,783 A | 5/1955 | Sullivan |
| 3,040,748 A | 5/1962 | Klein et al. |
| 3,080,564 A | 3/1963 | Strekopitov et al. |
| 3,193,165 A | 7/1965 | Akhalaya et al. |
| 3,217,557 A | 11/1965 | Martinot |
| 3,252,643 A | 5/1966 | Strekopytov et al. |
| 3,254,650 A | 6/1966 | Collito |
| 3,254,651 A | 6/1966 | Collito |
| 3,269,630 A | 8/1966 | Fleicher |
| 3,276,710 A | 10/1966 | Zernov et al. |
| 3,388,847 A | 6/1968 | Kasulin et al. |

(List continued on next page.)

FOREIGN PATENT DOCUMENTS

| DE | 1250709 | 7/1961 |
| DE | 3115835 | 10/1982 |
| DE | 4222251 | 1/1994 |
| EP | 0137685 | 4/1985 |
| EP | 107868 B1 | 9/1986 |
| EP | 0 419 660 A1 | 1/1990 |

(List continued on next page.)

OTHER PUBLICATIONS

Androsov, "New Method of Surgical Treatment of Blood Vessel Lesions" (1956) Arch. Surg. 73:902–910.
Berggren et al., "Clinical Experience with UNLINK 3M Precise Mincrovascular Anastomotic Device" Scand J Plast Reconstru Hand Surg. 1993127:35–39.
Cooper et al., "Development of the Surgical Stapler with Emphasis on Vascular Anastomosis," NY Acad. Sci, 1963;25–365–377.

(List continued on next page.)

*Primary Examiner*—Scott A. Smith
(74) *Attorney, Agent, or Firm*—Brian Tomko

(57) ABSTRACT

A stapler for stapling a tubular structure to another structure. The stapler has an anvil which is expandable from a collapsed position to an expanded position. The stapler has a recess which receives at least a portion of the tubular structure and a shoulder which receives an everted end of the tubular structure. A first actuator moves the anvil relative to the shoulder for compressing the structures which are to be stapled together. A second actuator is used for driving the staples through the structures to be stapled together.

19 Claims, 26 Drawing Sheets

U.S. PATENT DOCUMENTS

| | | |
|---|---|---|
| 3,452,615 A | 7/1969 | Gregory |
| 3,494,533 A | 2/1970 | Green et al. |
| 3,519,187 A | 7/1970 | Kapitanov |
| 3,552,626 A | 1/1971 | Astafiev et al. |
| 3,570,497 A | 3/1971 | Lemole |
| 3,589,589 A | 6/1971 | Akopov |
| 3,593,903 A | 7/1971 | Astafiev et al. |
| 3,638,652 A | 2/1972 | Kelley |
| 3,692,224 A | 9/1972 | Astafiev et al. |
| 3,774,615 A | 11/1973 | Lim et al. |
| 3,805,793 A | 4/1974 | Wright |
| 3,915,399 A | 10/1975 | Kron et al. |
| 4,009,841 A | 3/1977 | Matalia |
| 4,076,162 A | 2/1978 | Kapitanov et al. |
| 4,166,466 A | 9/1979 | Jarvik |
| 4,304,236 A | 12/1981 | Conta et al. |
| 4,319,576 A | 3/1982 | Rothfuss |
| 4,325,376 A | 4/1982 | Klieman et al. |
| 4,350,160 A | 9/1982 | Kolesov et al. |
| 4,352,358 A | 10/1982 | Angelchik |
| 4,366,819 A | 1/1983 | Kaster |
| 4,368,736 A | 1/1983 | Kaster |
| 4,466,436 A | 8/1984 | Lee |
| 4,505,414 A | 3/1985 | Filipi |
| 4,523,592 A | 6/1985 | Daniel |
| 4,553,542 A | 11/1985 | Schenck et al. |
| 4,573,468 A | 3/1986 | Conta et al. |
| 4,576,167 A | 3/1986 | Noiles |
| 4,586,503 A | 5/1986 | Kirsch et al. |
| 4,592,354 A | 6/1986 | Rothfuss |
| 4,593,693 A | 6/1986 | Schenck |
| 4,603,693 A | 8/1986 | Conta et al. |
| 4,607,637 A | 8/1986 | Berggren et al. |
| 4,624,255 A | 11/1986 | Schenck et al. |
| 4,624,257 A | 11/1986 | Berggren et al. |
| 4,646,745 A | 3/1987 | Noiles |
| 4,657,019 A | 4/1987 | Walsh et al. |
| 4,665,906 A | 5/1987 | Jervis |
| 4,700,703 A | 10/1987 | Resnick et al. |
| 4,703,887 A | 11/1987 | Clanton et al. |
| 4,747,407 A | 5/1988 | Liu et al. |
| 4,763,851 A | 8/1988 | Flament |
| 4,817,916 A | 4/1989 | Rawstron |
| 4,907,591 A | 3/1990 | Vasconcelloos et al. |
| 4,917,087 A | 4/1990 | Walsh et al. |
| 4,917,090 A | 4/1990 | Berggren et al. |
| 4,917,091 A | 4/1990 | Berggren et al. |
| 4,921,212 A | 5/1990 | deQuay |
| 4,936,942 A | 6/1990 | Sollinger et al. |
| 4,957,499 A | 9/1990 | Lipatov et al. |
| 5,119,983 A | 6/1992 | Green et al. |
| 5,197,649 A | 3/1993 | Bessler et al. |
| 5,234,447 A | 8/1993 | Kaster et al. |
| 5,242,457 A | 9/1993 | Akopov |
| 5,271,543 A | 12/1993 | Grant et al. |
| 5,292,053 A | 3/1994 | Bilotti et al. |
| 5,324,447 A | 6/1994 | Lam et al. |
| 5,330,157 A | 7/1994 | Dern et al. |
| 5,330,503 A | 7/1994 | Yoon |
| 5,333,773 A | 8/1994 | Main et al. |
| 5,336,233 A | 8/1994 | Chen |
| 5,348,259 A | 9/1994 | Blanco et al. |
| 5,366,462 A | 11/1994 | Kastger et al. |
| 5,395,030 A | 3/1995 | Kuramoto et al. |
| 5,403,333 A | 4/1995 | Kaster et al. |
| 5,478,354 A | 12/1995 | Tovey et al. |
| 5,522,834 A | 6/1996 | Fonger et al. |
| 5,549,619 A | 8/1996 | Peters et al. |
| 5,554,162 A | 9/1996 | DeLange |
| 5,588,479 A | 12/1996 | Schmut et al. |
| 5,620,452 A | 4/1997 | Yoon |
| 5,669,918 A | 9/1997 | Balazs et al. |
| 5,855,312 A | 1/1999 | Toledano |
| 5,868,760 A | 2/1999 | McGuckin, Jr. |
| 5,881,943 A | 3/1999 | Heck et al. |
| 5,947,363 A | 9/1999 | Bolduc et al. |
| 6,040,748 A | 3/2000 | Gueissaz |
| 6,248,117 B1 * | 6/2001 | Blatter ..................... 606/153 |
| 6,402,008 B1 * | 6/2002 | Lucas ..................... 227/175.1 |
| 6,485,496 B1 * | 11/2002 | Suyker et al. .............. 606/153 |

FOREIGN PATENT DOCUMENTS

| | | |
|---|---|---|
| EP | 0 384 647 A1 | 8/1990 |
| EP | 0419 660 A1 | 3/1991 |
| FI | 88386 | 12/1988 |
| FR | 1518083 | 3/1968 |
| FR | 1518083 A61b | 12/1968 |
| GB | 935490 | 9/1959 |
| GB | 2038692 | 7/1980 |
| GB | 2108418 | 5/1983 |
| NL | 7711347 | 4/1979 |
| NL | 8802966 A | 12/1988 |
| SU | 1038667 A | 2/1982 |
| SU | 995765 | 2/1983 |
| SU | 1097301 | 6/1984 |
| WO | WO 86/07122 A1 | 12/1986 |
| WO | WO 93/07408 A1 | 4/1993 |

OTHER PUBLICATIONS

Gentili et al.. "A Technique for Rapid Non–suture Vascular Anastomosis," Can. J. Neuro Sci., 10987;14(1):92–95.

Goetz et al., "Internal Mammary–coronary Artery Anastomosis: A Nonsuture Method Employing Tantalum Rings," J Thorac Card Surg. 1961;41(3):378–386.

Gottlob et al., "Anastomoses of Small Artenes and Veins by Means of Bushings and Adhesive," J Card Surg, 1968;9:337–341.

Guyton et al., "A Mechanical Device for Sutureless Aorta–Sapheneous Vein Anastomosis," Ann Thorac Surg, 1979;28:342–345.

Holt et al., "A New Technique for End–to–End Anastomosis of Small Arteries," Surgical Forum, v. 11, 1960, pp. 242–243.

Holt et al., "A New Method for Microvascular Anastomosis: Report of Experimental and Clinical Research," The American Surgeon, 1992;58(12):722–727.

Inokuchi, "A new type of vessel–suturing apparatus," (1958) AMA Arch. Surg. 77:954–957.

Inokuchi, "Stapling device for end–to–side anastomosis of blood vessels" (1961) arch. Surg. 82:27–31.

Kirsch et al., "A New Method for Microvascular Anastomosis: Report of Experimental and Clinical Research," The American Surgeon, vol. 58, No. 123, Dec. 1992, pp. 722–727.

Kirsch et al., "A New Technique for End–to–end Anastomosis of Small Arteries" Surgical Forum, 1960;11:242–243.

Lanzetta et al., "Long–term Results of 1 Milimeter Arterial Anastomosis Using the 3M Precise Microvascular Anastomotic System," Microsurgery; 1992; 13:313–320.

Li et al., "End–to–side–anastomosis in the Dog using the 3M Precise Microvascular Anastomotic System: A Comparative Study," J. Reconstruct Microsurg, 1991;7(4):345–350.

Miller, "The Russian Stapling Device," New York Sci., 1963,25:378–381.

Nakayama et al., "A Simple New Apparatus for Small Vessel Anastomosis (free autograft of the sigmoid included)," Surgery, 1962;52(6):918–931.

Narter et al., "An Experimental Method for Nonsuture Anastomosis of the Aorta," Surg Gyne & Obs, 1964;632–361.

Olearchyk, "Vasilli I Kolesov—a Pioneer of Coronary Revascularization by Internal Mammary–coronary Artery Grafting," J Thorac. Surg, 1988;96(1)13–18.

Ragnarsson et al., "Microvenous End–to–side Anastomosis; An experimental Study Comparing the UNILINK System and Sutures," J. Reconstruct Microsurg. 1989;5(3):217–224.

Ragnarsson et al., "Arterial End–to–side Anastomosis with the UNILINK System," Ann Plastic Surg, 1989;22(3): 405–415.

Rohman et al., "Double coronary artery–internal mammary artery anastomoses, tantalum ring technique," (1960) Surg. Forum 11:236–243.

Vogelfanger et al. "A concept of automation in vascular surgery: a preliminary report on a mechanical instrument for arterial anastomosis," (1958) Can. J. Surg. 58:262–265.

* cited by examiner

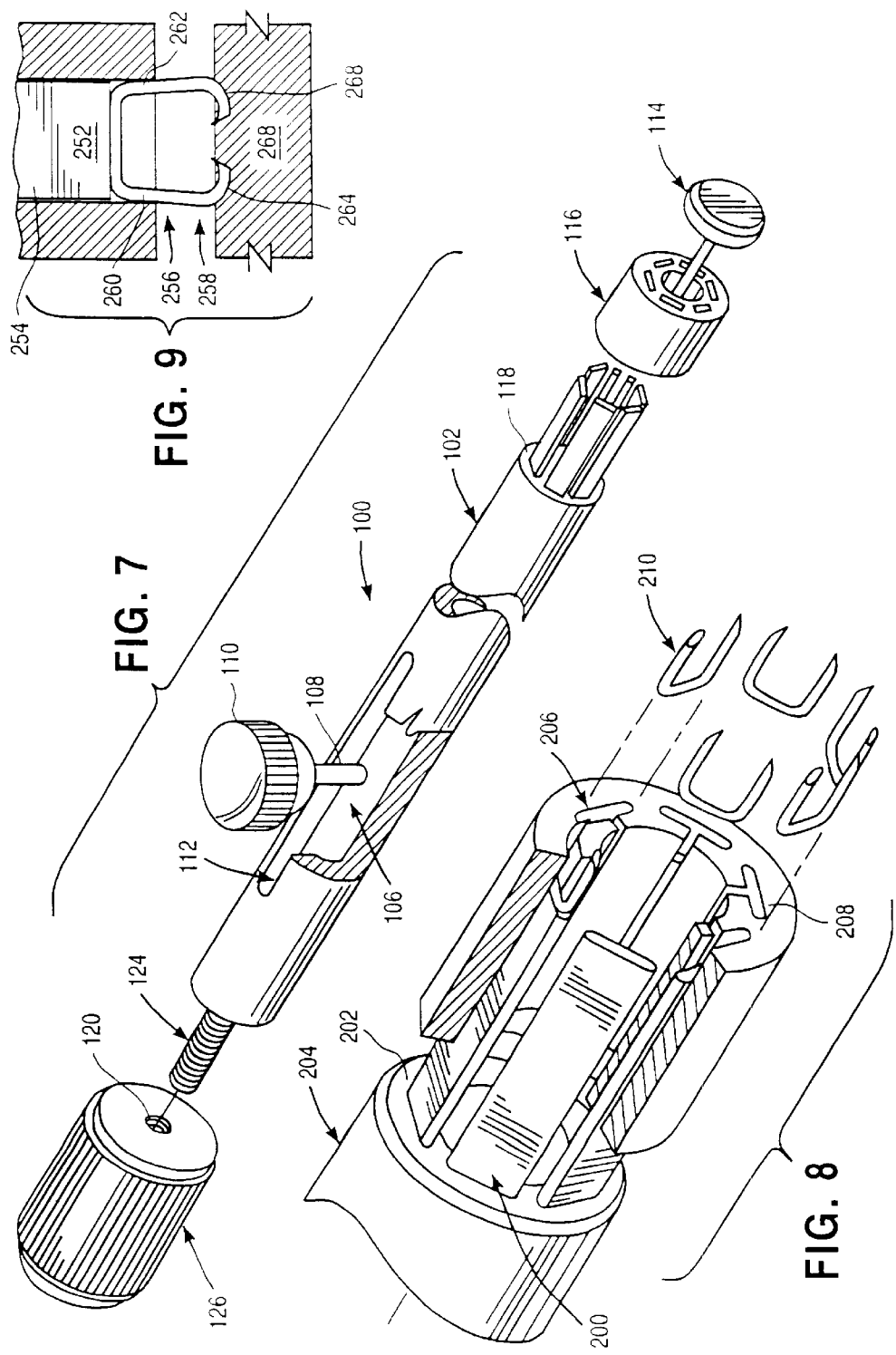

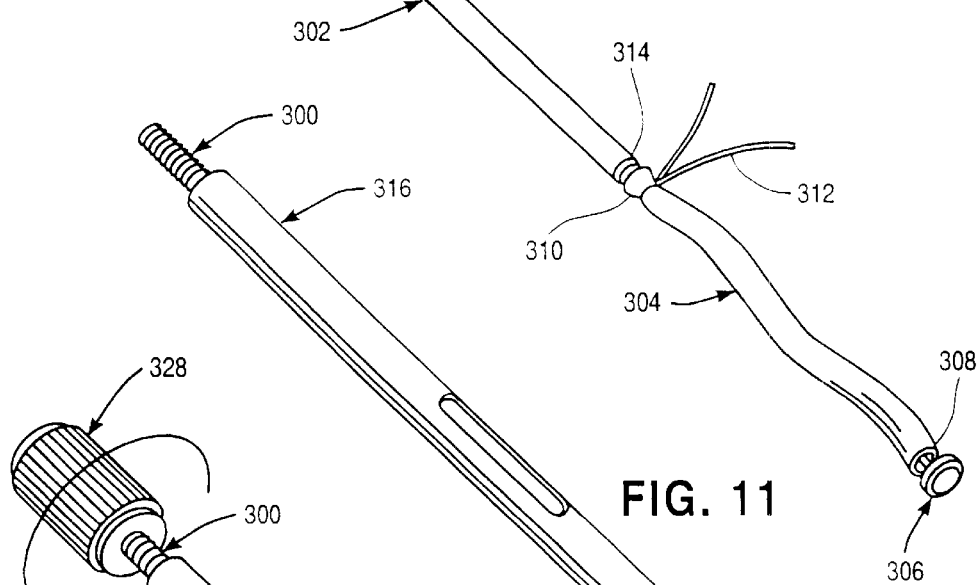
FIG. 10
FIG. 11
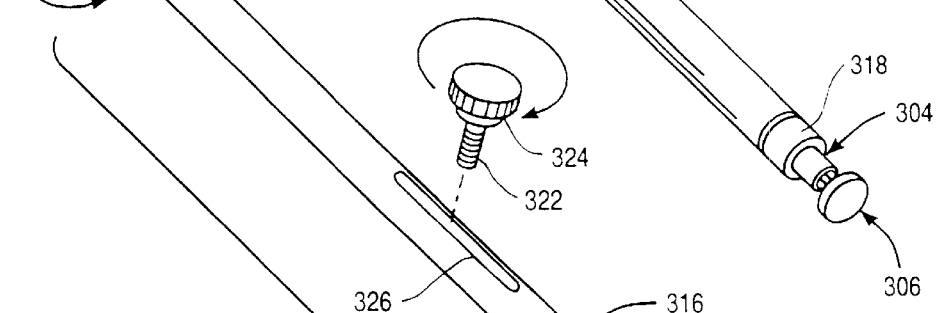
FIG. 12

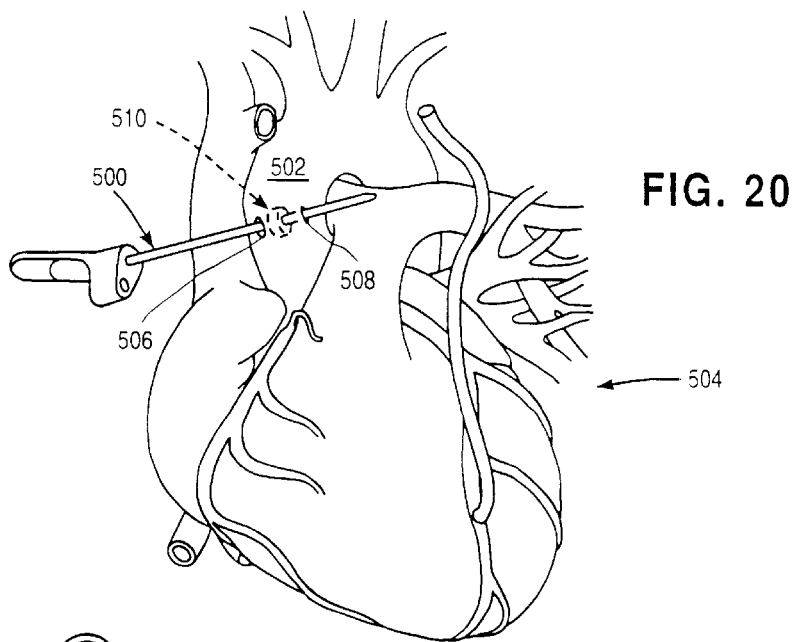
FIG. 20
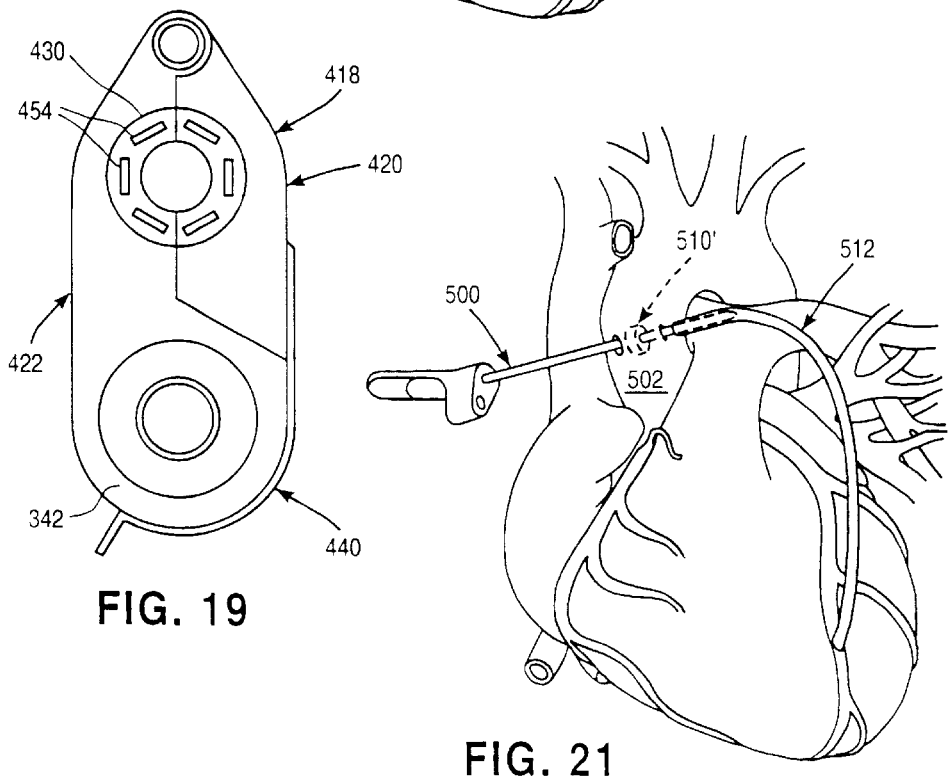
FIG. 19
FIG. 21

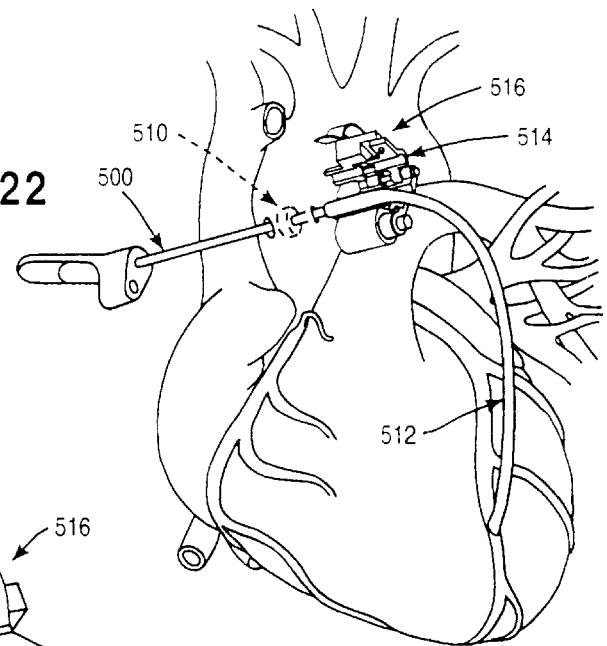
FIG. 22
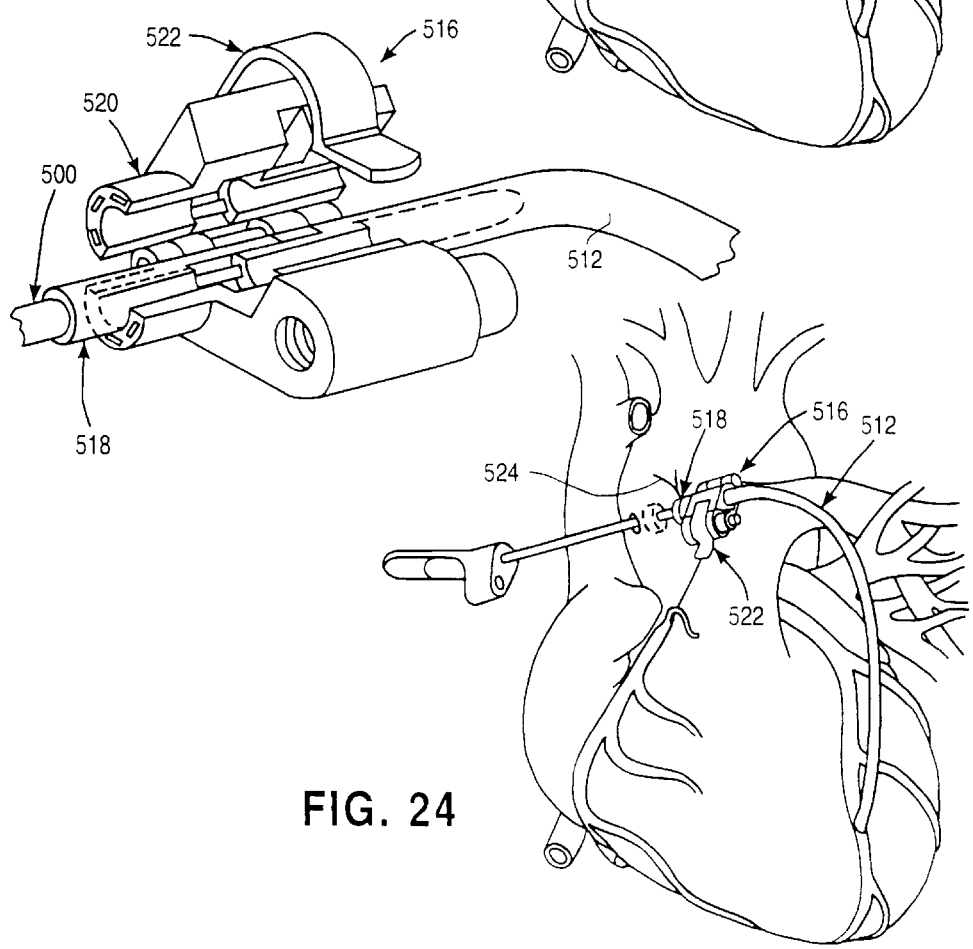
FIG. 23
FIG. 24

SURGICAL STAPLING INSTRUMENT AND METHOD THEREOF

CROSS REFERENCE TO RELATED APPLICATIONS

This application is a continuation U.S. application Ser. No. 09/776,612, filed Feb. 2, 2001, now U.S. Pat. No. 6,588,643 which is a continuation of U.S. application Ser. No. 09/391,297, filed Sep. 7, 1999, issued on Apr. 4, 2001, as U.S. Pat. No. 6,209,773, which is a continuation of U.S. application Ser. No. 09/045,673, filed on Mar. 20, 1998, issued on Sep. 7, 1999 as U.S. Pat. No. 5,947,363, which is a continuation of U.S. application Ser. No. 08/597,691, filed on Feb. 6, 1996, now issued as U.S. Pat. No. 5,732,872, which is a continuation-in-part of U.S. application Ser. No. 08/550,285, filed on Oct. 31, 1995, now issued on Jan. 20, 1998 as U.S. Pat. No. 5,709,335, which is a continuation of U.S. application Ser. No. 08/261,167 filed on Jun. 17, 1994, now abandoned, the full disclosures of which are hereby incorporated by reference.

FIELD OF THE INVENTION

The invention relates generally to surgical stapling appliances and more particularly to an improved apparatus and method for the anastomotic surgical stapling of luminal organs, such as vascular lumens.

BACKGROUND OF THE INVENTION

Various instruments are known in the prior art for end-to-end and end-to-side anastomotic surgical stapling together of parts of the alimentary canal (i.e., esophagus, stomach, colon, etc.). These instruments employ staple cartridges, generally in the shape of a hollow cylinder, of different sizes to accommodate tubular organs of varying diameters. End-to-end and end-to-side anastomoses are achieved by means of at least one ring of surgical staples.

The traditional technique for surgical stapling anastomosis is to position the stapling cartridge within the tubular organ to be stapled. The cut end of the tubular organ is inverted (i.e., folded inwardly) over the annular end of the staple cartridge creating an inverting anastomosis upon stapling. An essential requirement of the inverting anastomotic technique is the incorporation of knives within the staple cartridge housing to trim excess tissue from the anastomotic connection.

The prior art anastomotic stapling instruments form generally circular anastomotic connections, and have been largely limited to alimentary organs. With respect to end-to-side vascular anastomosis, circular connections, rather than an elliptical connections, are sometimes disadvantageous as they are less physiologic or natural. This unnatural connection may create turbulence in the blood flow as it courses through the anastomosis, damaging the intima (i.e., inner wall) of the blood vessel and predisposing it to forming blood clots.

In the present state of the art, end-to-end and end-to-side anastomosis between blood vessels have typically been accomplished by hand-sewn suturing techniques. These techniques are time consuming, not as reliable as stapling, and subject to greater human error than stapling. Current stapling instruments used for alimentary canal are not suitable, however, for vascular anastomosis due to their large sizes and inability to provide non-circular and low turbulence anastomoses. A typical prior art instrument has a circumference of approximately 8 cm (3 in), far too thick to accommodate coronary arteries and veins, which have circumferences ranging from 0.50 to 1.0 cm and from 1.5 to 2.5 cm, respectively.

An additional drawback of prior stapling instruments is the inability to provide an everted (i.e., folded outwardly) anastomosis. An inverted vascular anastomosis would expose the cut ends of the blood vessels to the vessel lumen and could lead to the formation of blood clots. For this reason, hand-sewn everted anastomoses for vascular connections are preferable, despite time and reliability drawbacks.

Accordingly, it is a general object of the present invention to provide an improved instrument and method for vascular anastomosis.

It is also an object of the present invention to provide a surgical stapling instrument small enough to accommodate vascular lumens.

Another object of the present invention is to provide a surgical stapling instrument for everted anastomosis.

Another object of the present invention is to provide a method for surgical stapling that does not require the removal of excess tissue from the anastomotical connection.

Still another object of the present invention is to provide an instrument and method for vascular anastomosis that is less time-consuming and more reliable than the prior art.

SUMMARY OF THE INVENTION

The present invention provides a novel instrument and method for vascular anastomoses which overcomes the drawbacks of prior art designs and achieves the aforesaid advantages.

Very generally, the surgical stapling instrument of the present invention is for stapling a tubular tissue structure having at least one distal end to a luminal structure, such as a vascular lumen or another tubular tissue structure. The instrument comprises a rod having a circumference sufficient to pass within the tubular tissue structure, an anvil mounted on the rod, and a generally tubular staple cartridge for containing a plurality of staples. The anvil has an array of staple deforming means thereon and is of a size sufficient to pass through a surgically formed opening in and to be accommodated within the luminal structure. The inner passage of the staple cartridge is sufficient to axially accommodate the tubular tissue structure between the rod and the inner surface of the staple cartridge, and sufficient to allow the staple cartridge to be moved axially along the rod. The staple delivery end of the staple cartridge is positioned toward the staple deforming means of the anvil and has an outer dimension small enough so that the tubular tissue structure can be everted thereover. A clamping mechanism secures the everted portion of the tubular tissue structure and the luminal structure adjacent to the surgically formed opening between the staple cartridge and the anvil. A plurality of staples may then be ejected to pass through the everted portion of the tubular tissue structure and the luminal structure to engage the staple deforming means to deform the staples and create a bond between the tubular tissue structure and the luminal structure.

BRIEF DESCRIPTION OF THE DRAWINGS

FIG. 7 is an exploded top perspective view, partially cut-away, of the anastomosis device of FIG. 1.

FIG. 8 is an enlarged, exploded, top perspective view, partially cut-away, of a staple cartridge assembly of the anastomosis device of FIG. 1.

FIG. 9 is an enlarged, side elevation view, in cross-section, of the anvil and staple cartridge assembly of the anastomosis device of FIG. 1 illustrating the deformation of a staple.

FIGS. 10–12 is a sequence of top perspective views illustrating the loading of a tubular tissue structure in the anastomosis device of FIG. 1

FIG. 19 is an end view of the staple cartridge assembly of FIG. 18.

FIGS. 20–22, 24, 25, 27 and 28 is sequence of top perspective views illustrating the application of the alternative embodiment anastomosis device of FIG. 17 for proximal anastomosis of the grafted tubular tissue structure to the ascending aorta.

FIGS. 23 and 26 is a sequence of fragmentary, top perspective views illustrating the loading of a tubular tissue structure in the alternative embodiment anastomosis device of FIG. 17.

DESCRIPTION OF THE PREFERRED EMBODIMENTS

Referring to FIGS. 1–7, there is shown a structural embodiment of the present invention which is best suited for anastomotic stapling of a tubular vessel having two distal or untethered ends. As will be evidenced by the detailed description below, this embodiment, i.e., distal stapler, is ideal for use during cardiopulmonary bypass surgery for making the primary anastomotic connection of a bypass vein to a coronary artery or to the aorta.

Figure 1:
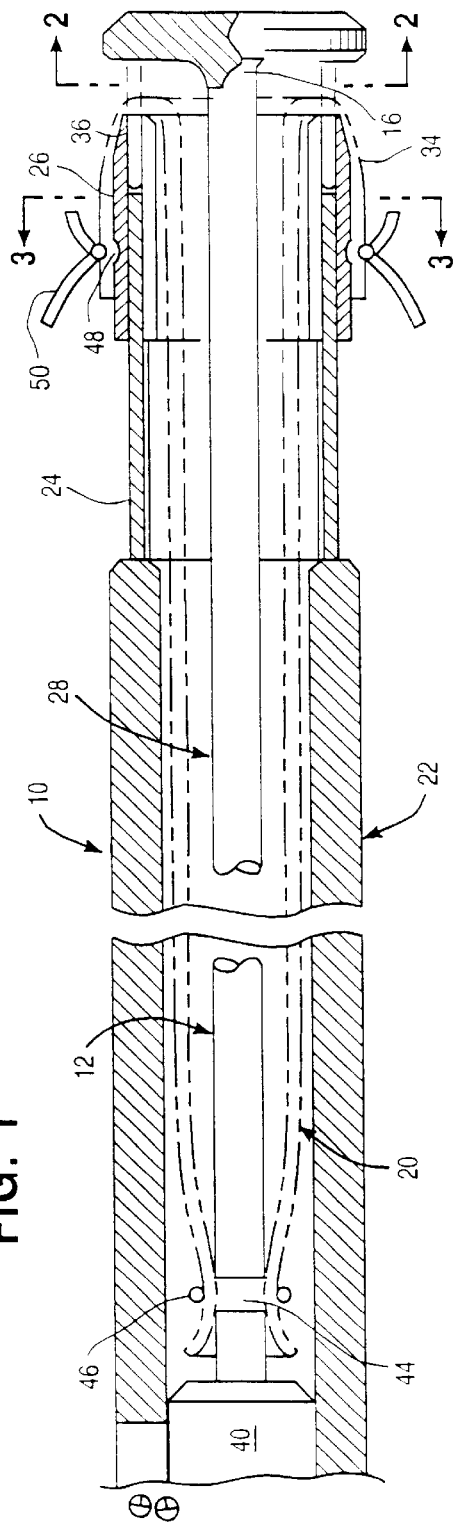
FIG. 1 is a fragmentary side elevation view, in cross section, of one embodiment of the anastomosis device constructed in accordance with the present invention and illustrating an end of the tubular tissue structure everted over the device end.

Referring now to FIG. 1, a portion 10 of the wholly configured distal stapler of the present invention, as shown in FIG. 7, comprises an elongated central rod 12 with anvil 14 mounted at its distal end 16. Anvil 14 is in the form of a circular, elliptical or tear drop-shaped disk and is mounted, by suitable means such as welding, to the end of central rod 12 transversely thereof and at the center of the anvil. The edges of anvil 14 are beveled or otherwise generally rounded to enable anvil 14 to slip easily through incisions in vascular walls—much like a button through a button hole.

The central rod 12 has a circumference sufficient to permit the rod to axially extend through a tubular vessel, indicated in phantom at 20, to be stapled. Central rod 12 also axially extends within tubular housing 22, driver pins 24 and staple cartridge 26, together forming a contiguous shaft 28 having an inner circumference sufficient to accommodate tubular vessel 20 sandwiched between them and central rod 12. Staple cartridge 26 has an outer circumference sufficient to accommodate everted end 34 of tubular vessel 20. Lip 36 of cartridge 26 is tapered to facilitate eversion of tubular vessel 20. Anvil 14 has circumference of a size equivalent to the outer circumference of staple cartridge 16.

Circumferences of vascular vessels range from 0.50 to 1.0 cm for coronary arteries and from 1.5 to 2.5 cm for veins. Accordingly, all circumferences, discussed above, of stapler 10 are of a size to optimally coaxially accommodate the vein to be stapled.

The end of central rod 12 opposite anvil 14 is centrally mounted, preferably welded, on a cylindrical base 40 which extends coaxially within tubular housing 22 (as shown in FIG. 7 by reference number 106) and has a circumference sufficient to be slidable within tubular housing 22. The accommodated tubular vessel 20 extends along central rod 12 to cylindrical base 40. Provided on the surface of central rod 12 proximal to base 40 is circumferential groove 44 for facilitating the securing of tubular vessel 20 to rod 12 by means of string 46. Similarly, circumferential groove 48 and string 50 are provided to secure everted end 34 of vessel 20 to staple cartridge 26. An alternative embodiment of staple cartridge 26 for securing an everted vein comprises tiny hooks around the circumference at end 36 of the cartridge. Other suitable means for accomplishing the securing function may be used as well.

Figure 2:
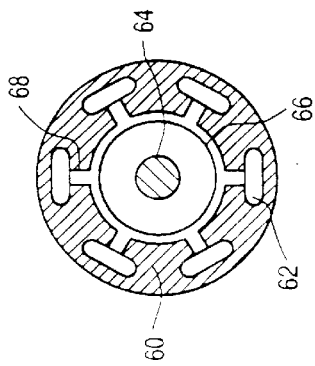
FIG. 2 is a front elevation view, in cross-section, of the anastomosis device taken substantially along the plane of the line 3—3 in FIG. 1

Referring now to FIG. 2, there is shown a cross-sectional view of stapler 10 of the present invention in the direction of arrows 2—2 of FIG. 1. Here, the staple delivery end 60 of a circular staple cartridge is illustrated encasing a circular array of staple delivery means or staple shafts 62. The present invention is not limited to a single staple shaft array, however. It is commonly known in the art to employ a plurality of concentric arrays or rows of staple shafts for anastomotic procedures. Extending from staple shaft array 62, is an array of narrow channels 68, each narrow channel corresponding to each staple shaft. Channel array 68 is used solely for manufacturing purposes and is not a necessary element of the invention. Central rod 64 and its base 66 are axially and centrally located within the cylindrical staple cartridge 60.

Figure 3:
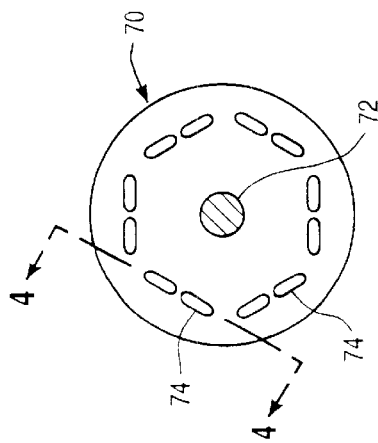
FIG. 3 is a rear elevation view, in cross-section, of the anastomosis device taken substantially along the plane of the line 2—2 in FIG. 1

FIG. 3 shows the underside view of anvil 70 in the direction of arrows 3—3 of FIG. 1. The anvil 70 has an array 74 of means for deforming staples. Central rod attachment 72 is centrally located on anvil 70 which provides an array of staple deforming means 74, comprised here of an array of recess pairs, for bending staples projected from corresponding array of staple shafts 62 of the staple cartridge of FIG. 2.

Figure 4:
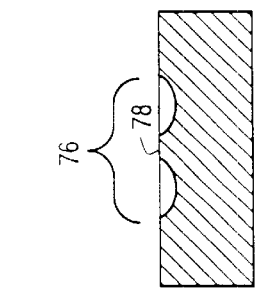
FIG. 4 is a side elevation view, in cross-section, of the anvil of the anastomosis device taken substantially along the plane of the line 4—4 in FIG. 3

Depicted in FIG. 4 is a cross-sectional view of anvil 70 in the direction of arrows 4—4 of FIG. 3. Each recess pair 76 is curved to bend staple legs radially inward. The projected staples can be made to bend radially inward or radially outward depending on the spacing 78 between the recess of each paired recess 76. Alternatively, each recess can be positioned orthogonal to its present position to bend the staple legs at right angles to their axis of projection.

Although the present invention is primarily described and depicted as forming staple bonds that are circular and as having component circumferences that are circular, other embodiments are realized for forming staple bonds having elliptical, tear drop or other generally oval circumferences. Accordingly, the anvil and associated staple recess array, and the cartridge housing and associated staple shaft array of these alternative stapler embodiments have circumferences in the shape of the desired staple bond. For example, FIGS. 5 and 6 illustrate an anvil and staple cartridge, respectively, having tear-drop shaped circumferences.

Figure 5:
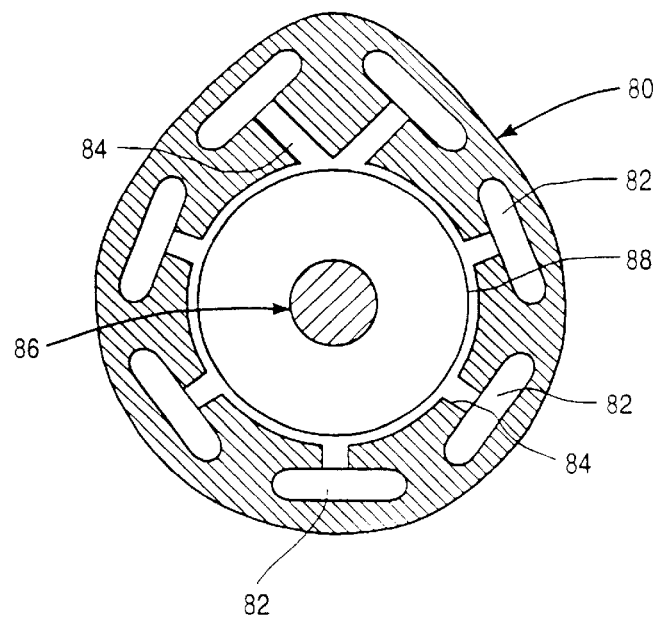
FIG. 5 is a front elevation view, in cross-section, of an alternative embodiment of FIG. 3 illustrating a tear drop-shaped configuration.

FIG. 5 shows a cross-sectional view of a tear-drop shaped staple cartridge. The staple delivery end 80 of the staple cartridge is illustrated encasing a tear drop array of staple delivery means or staple shafts 82. Extending from staple shaft array 82, is an array of narrow channels 84, each narrow channel corresponding to each staple shaft. Channel array 84 is used solely for manufacturing purposes and is not a necessary element of the invention. Central rod 86 and its base 88 are coaxially and centrally located within the cylindrical portion of dear drop staple cartridge 80.

Figure 6:
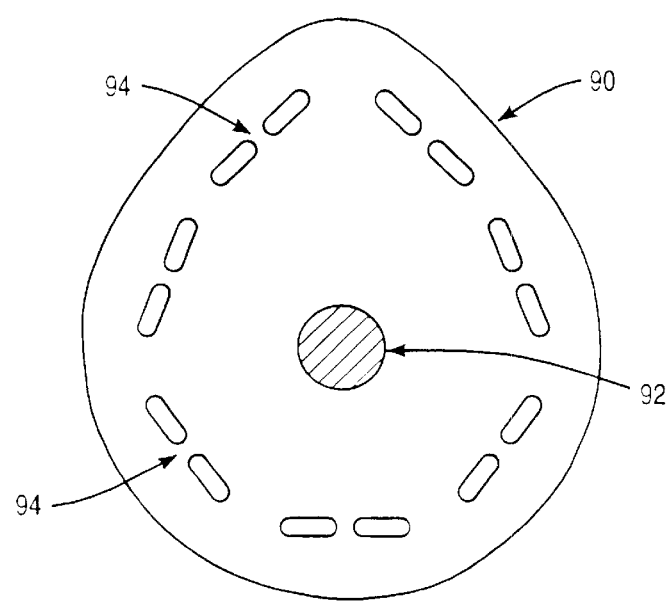
FIG. 6 is a rear elevation view, in cross-section, of the anvil of the alternative embodiment of FIG. 5 taken substantially along the plane of the line 2—2 in FIG. 1

FIG. 6 shows the underside view of a tear drop shaped anvil 90. Central rod attachment 92 is centrally located on the circular portion of anvil 90 which provides an array of staple deforming means comprised of recess pairs 94 for bending staples projected from corresponding array of staple shafts 82 of the staple cartridge of FIG. 5.

Referring now to FIG. 7, there is shown stapler 100 of the same embodiment depicted in FIGS. 1–4. A tubular housing 102 coaxially contains central rod 104 and rod base 106, the end of central rod 104 opposite that of anvil 114 being suitably mounted, such as by welding, to rod base 106 (connection not shown). Threadedly mounted to and extending perpendicular from rod base 106 is a short stem 108, positioned at approximately half the length of base 106. The top of stem 108 has cylindrical knob 110 transversely mounted. Stem 108 is moveable within narrow channel 112, cut within housing 102 and running parallel to the axis traveled by central rod 104 and rod base 106. Channel 112 limits the rotational movement of stem 108 and thereby maintains a proper radial orientation between anvil 114 and staple cartridge 116 during reciprocation.

Weldedly mounted to and protruding perpendicularly from cylindrical face 118 of housing 102 and paralleling rod 104 is cylindrical array of staple driver pins 120, all drivers pins being identical and each having the form of a solid parallelogram. Staple cartridge 116 encases, from end to end, cylindrical array of hollow staple shafts 122 which holds a plurality of preloaded staples (not pictured). All shafts 122 are identical and each has height and width dimensions such that a corresponding staple driver pin 120 is slidable therein.

In order to have an optimally functioning stapler, it is necessary to maintain a clean and clear passageway for central rod 104, base 106 and staple shafts 122. Accordingly, one embodiment of the present invention comprises a disposable cartridge which is disposed of and replaced after one anastomotic stapling. Another embodiment provides a slidable sleeve around the driver pin array to prevent blood and tissue from getting caught therein.

For anastomosis to be successful, it is imperative not to injure the living tissue being stapled by overcompressing it between anvil 114 and staple cartridge 116 or by a staple bond that is exceedingly tight. Accordingly, overcompression of the tissue is prevented in the present invention by limiting the length of driver pins 118. Other embodiments are known in the prior art for accomplishing this objective. For example, U.S. Pat. No. 4,575,468 employs mutually coacting stops located on the inner surface of a tubular housing and on the surface of a coaxial rod to provide variable degrees of engagement between tissues to be stapled so as to ensure against overcompression of the tissue. A spring-loaded engagement between the rod and tubular housing is also applicable for the present invention. Other means suitable for this purpose will be apparent to those having ordinary skill in the art.

Finally, FIG. 7 illustrates threaded end 124 of rod base 106 which extends beyond the length of housing 102 to threadedly engage with cylindrical nut 126 which has internally threaded throughbore 120 extending the full length of cylindrical nut 126 to allow end 124 to exit therethrough.

FIGS. 8 and 9 illustrate the mechanical interaction between the staple driver, staple cartridge and anvil upon engagement. FIG. 8 illustrates staple driver array 200 mounted on face 202 of tubular housing 204 slidably engaged within staple shaft array 206 of staple cartridge 208. Staple array 210 is projected from staple cartridge 208 and through the tissues to be stapled (not shown). FIG. 9 shows a close-up of a staple being driven by driver pin 252 and projecting through cartridge 254 through tissues 256 and 258. The legs 260 and 262 of staple 250 then engage with and bend along the curved recesses 264 and 266, respectively, of anvil 268 to form a bond between tissues 256 and 258.

Referring now to FIGS. 10–16, with like numbers referring to like elements, there is illustrated the steps of the anastomotic procedure using the structural embodiment described above. Now referring to FIG. 10 specifically, the anvil-headed end of rod base 302 is inserted into transected vein 304 having a length in the range of 10–18 cm (4–7 inches). End 308 (the end to be stapled) of vein 304 is positioned proximate to anvil 306. Opposing end 310 of vein 304 is tied with string 312 to central rod 314 at a circumferential depression (not shown) proximate to base 302.

Figures 13, 14, 15:
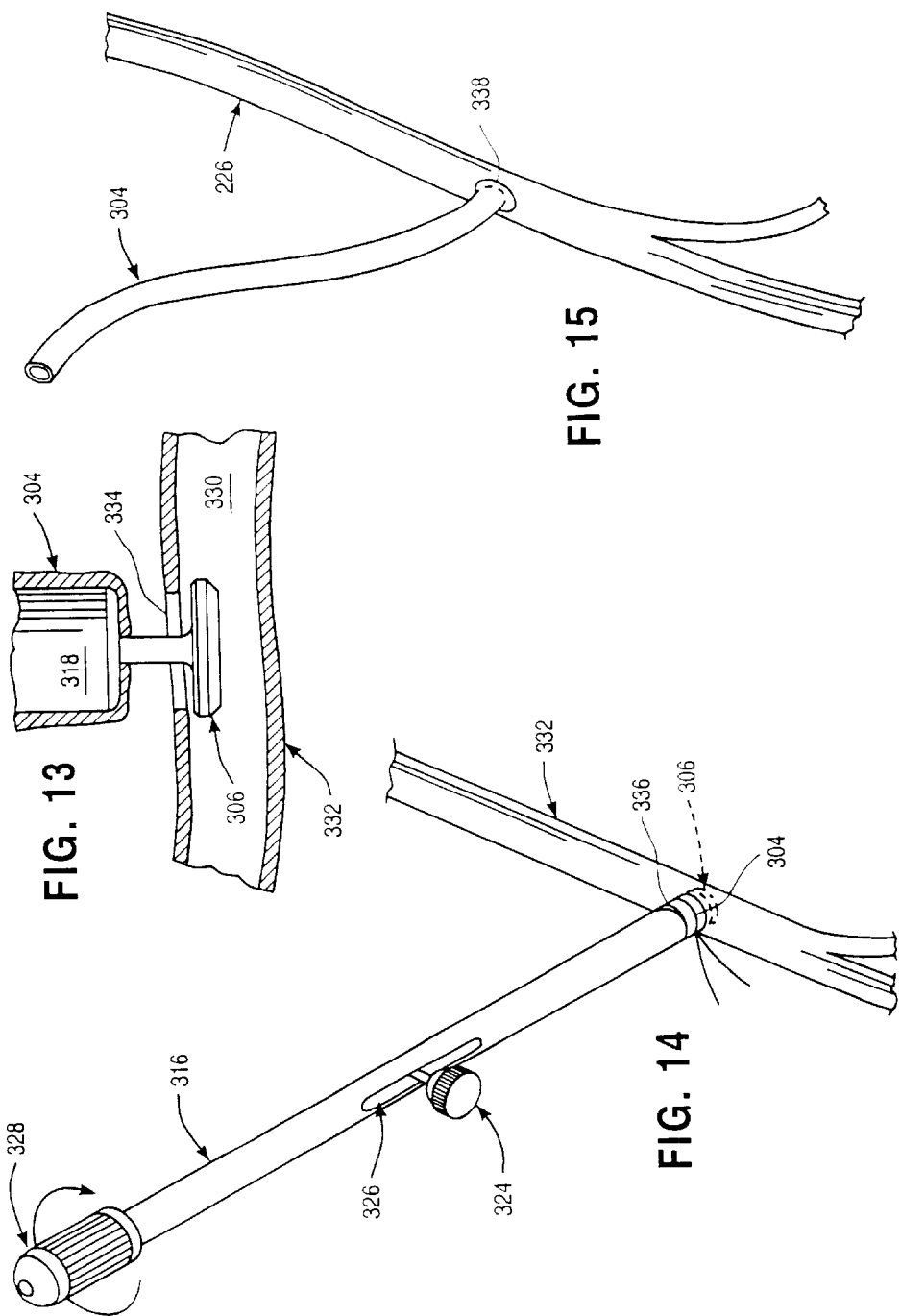
FIG. 13 is an enlarged, side elevation view, in partial cross-section, showing the positioning of the anvil of the anastomosis device through a luminal structure.
FIG. 14 is a reduced top perspective view of the anastomosis device of FIG. 1 mounted to the luminal structure.
FIG. 15 is a reduced top perspective view of the tubular tissue structure anastomotized to the luminal structure using the anastomosis device of FIG. 1.

FIG. 11 shows the step of inserting central rod 314 with attached vein 304 into staple cartridge 318 and tubular housing 316 such that staple cartridge 318 is proximate to anvil 306. FIG. 12 illustrates the next several steps of the method of the present invention which can be performed in any order. The end of vein 304 is everted over staple cartridge 318 and tied with string 320 securing it to staple cartridge 318 (covered by vein 304). Threaded stem 322 of cylindrical knob 324 is threadedly engaged with a threaded bore (not shown) base 302, the bore being aligned with narrow channel 326. Cylindrical nut 328 is threadedly engaged with the threaded end 300. As indicated in FIG. 13, anvil 306 is positioned within lumen 330 of vascular artery 332 via incision 334. A cross-section of a portion of vein 304 is shown everted over the staple delivery end of staple cartridge 318.

In FIG. 14, central rod 314 (not visible) and rod base 302 (not visible) are optimally coaxially positioned within tubular housing 316 by means of sliding knob 324 along channel 326 toward vascular artery 332. Nut 328 is rotated in a clockwise direction to engage it with tubular housing 316 causing rod base 302 to become rigidly interconnected with nut 328. As the clockwise turning continues, rod base 302 is drawn through the bore in nut 328, bringing the staple cartridge 336 and anvil 306 within artery 332 together. An embodiment employing mutually coacting stops (not shown) would, at this point, be at the first coacting position or the "loaded" position. The clockwise motion is continued so that everted vein 304 engages with the wall of artery 332 and until the staple drivers (not visible) are actuated, driving the staples (not visible) through the tissues to create a bond 338 (FIG. 15). If mutually coacting stops are employed, the configuration would be in the "firing" position.

Figure 16:
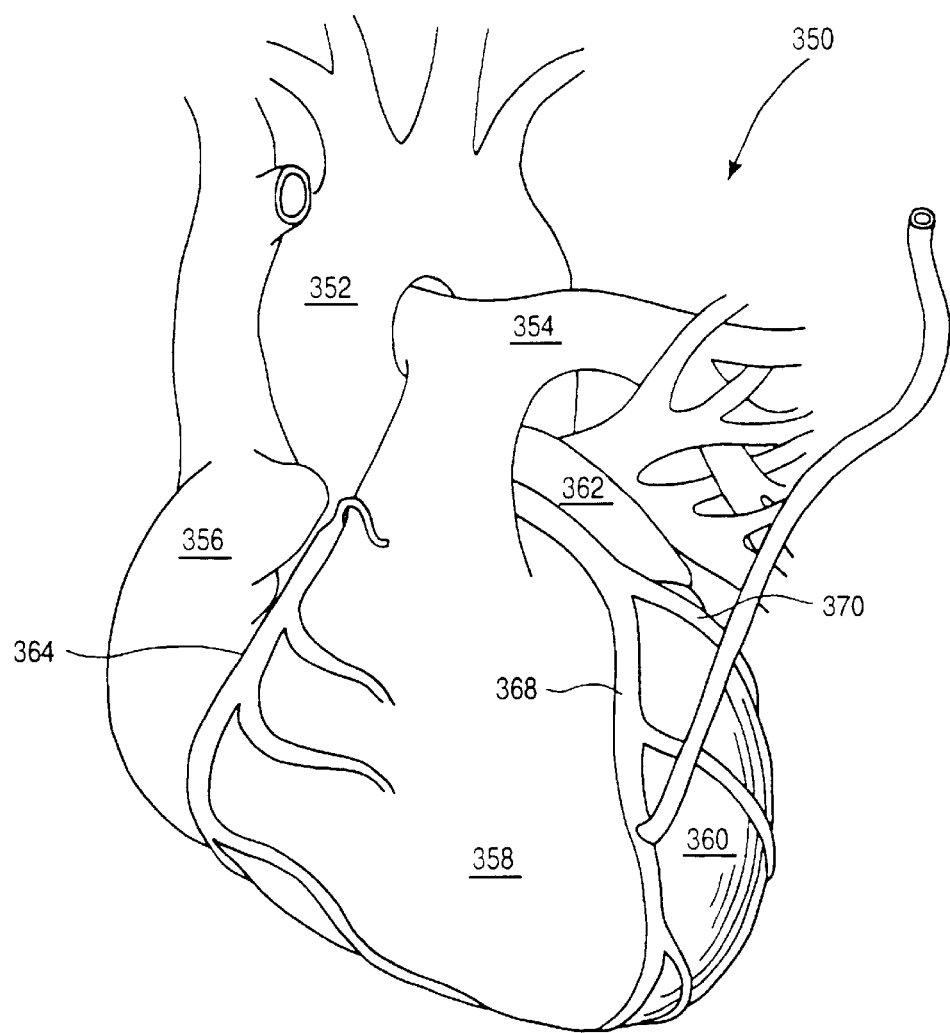
FIG. 16 is a front elevation view of a grafted tubular tissue structure anastomotized to a coronary artery of the heart through the anastomosis device of FIG. 1.

Finally, FIG. 16 illustrates heart 350 having aorta 352, pulmonary artery 354, right atrium 356, right ventricle 358, left ventricle 360, left atrial appendage 362, right coronary artery 364, left anterior descending artery 368, and diagonal artery 370. Here, vein 304 has been anastomotically stapled to left anterior descending artery 368.

To complete the anastomotic procedure of the bypass vein 304, the unstapled end of the anastomotized vein 304 must now be connected to aorta 352.

However, another structural embodiment of the present invention, referred to as the "proximal" stapler, is needed since the embodiment described above, i.e., the "distal" stapler, requires the vein to have two distal or untethered ends. Accordingly, FIGS. 17–28 describe a structure and method thereof for a second embodiment of the present invention which is suited for the anastomotic stapling of a tubular vessel having only one distal end, the other end having already been anastomotically stapled.

Figure 17:
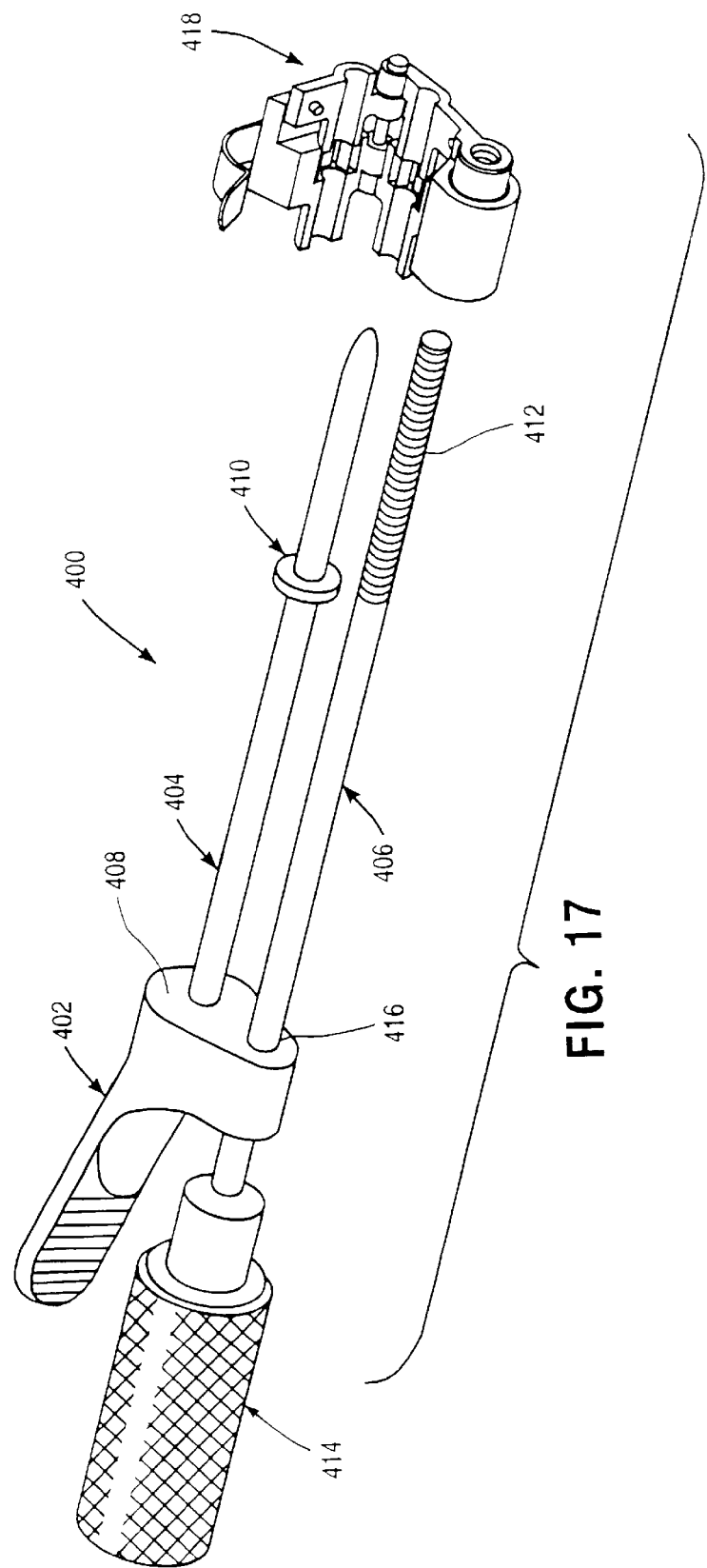
FIG. 17 is an exploded top perspective view of an alternative embodiment of the anastomosis device of the present invention.
Figure 18:
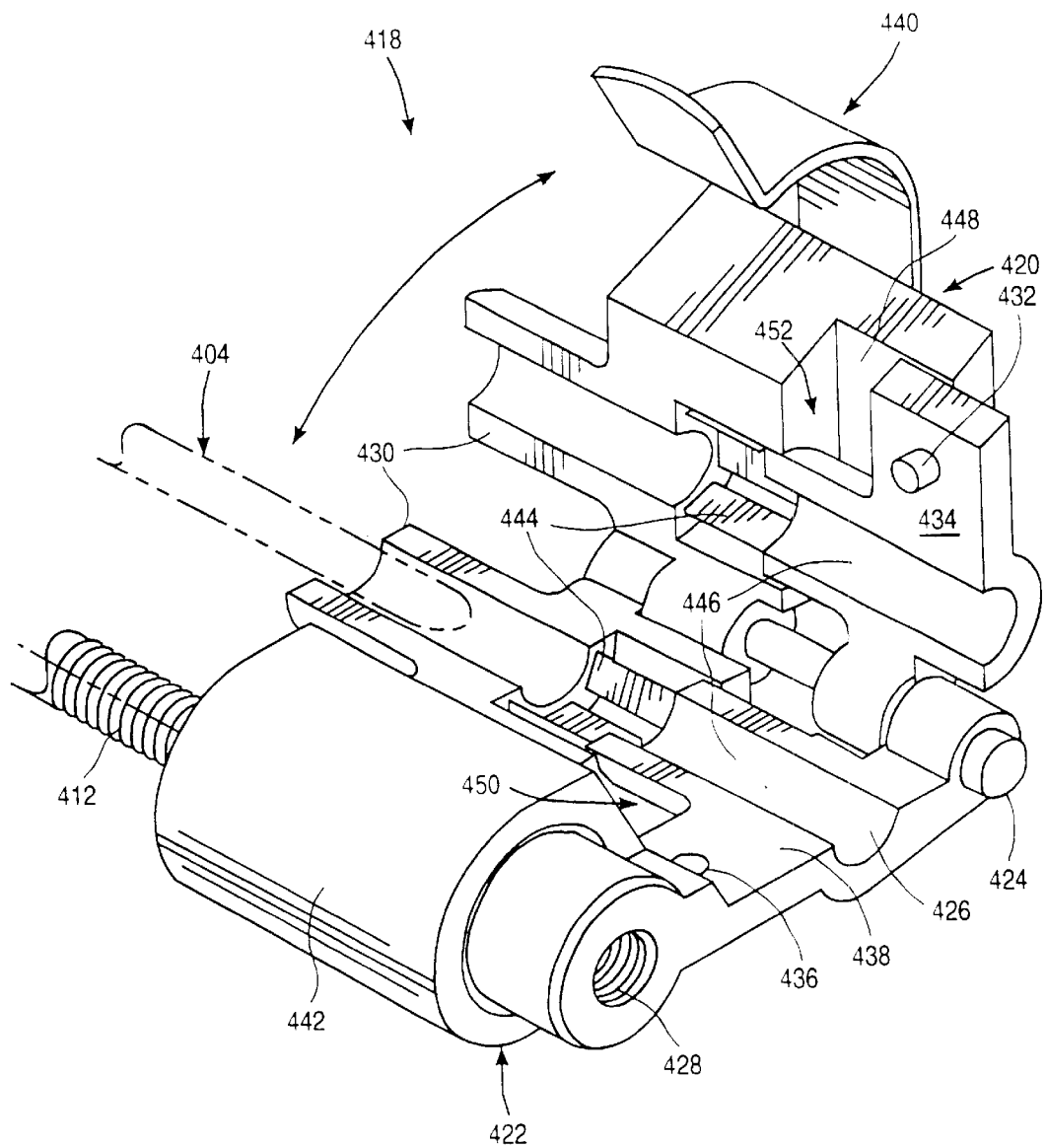
FIG. 18 is a fragmentary, enlarged top perspective view of a staple cartridge assembly of the alternative embodiment anastomosis device of FIG. 17.

Referring now to FIGS. 17–19, with like numbers referencing like elements, there is shown anastomotic stapler 400 having handle 402 with elongated vessel rod 404 and elongated driver rod 406 mounted perpendicularly to handle face 408 and parallel to each other, both being of approximately the same length. Vessel rod 404 has a centrally mounted generally circular anvil 410. Vessel rod 404 has a circumference sufficient to coaxially accommodate a tubular vessel (not shown) to be stapled to the aorta. Driver rod 406, having threaded end 412 and handle 414, extends through bore 416 of handle 402.

Stapler 400 also comprises staple cartridge 418, enlarged in FIG. 18 for purposes of describing its detail. Referring then to FIG. 18, there is shown the staple cartridge of FIG. 17 in its open position having top and bottom units 420 and 422, respectively. Units 420 and 422 are engaged at one side by hinge 424 which allows cartridge 418 to be opened and closed. Staple cartridge 418 has two parallel bores 426 and 428 with inner circumferences sufficient to coaxially accommodate vessel rod 404 with a coaxially accommodated vein (not shown) and driver rod 406, respectively. Staple delivery end 430 extends from staple cartridge 418 along the axis of bore 426 to accommodate the everted end of a vein to be stapled. Bore 428 is internally threaded to be threadedly engagable with driver rod end 412.

For a proper fit between units 420 and 422, a detent-recess pair is provided having detent 432 extending from inner surface 434 of top unit 420 which mates with recess 436 within inner surface 438 of bottom unit 422. To secure closing, a curved clip 440 is provided to fit around cylindrical casing 442 of bore 428.

When in a closed position, staple cartridge 418 has cylindrical staple delivery means or staple shaft array (not shown) encased in staple delivery end 430 which mates with cylindrical driver pin array 444 mounted on driver 446. Both the hollow shafts and the solid driver pins have height and width measurements that allow them to be slidably engageable with each other. Driver 446 is slidable along surface 448 of top unit 420 and surface 450 of bottom unit 422 to the point of engagement with shoulder 452 of top unit 420 upon which driver pin array 444 becomes engaged within the staple shaft array projecting preloaded staples from the end of staple delivery end 430. Shoulder 452 limits the engagement of driver pin array 444 so that the tissue being stapled is not overcompressed. Modifications of the this embodiment can employ mutually coacting stops or spring-loaded type configurations between the driver and staple cartridge to prevent against overcompression of the tissue.

FIG. 19 shows a front view of staple cartridge 418 in its closed position with top unit 420 engaged with bottom unit 422. Clip 440 securely fits around cylindrical casing 442. Staple deforming end or staple shaft array 454 is shown on the face of staple delivery end 430.

FIGS. 20–28, with like numbers referencing like elements, depict the various steps of the anastomotic procedure using the structural embodiment in FIGS. 17–19 described above. Referring now to FIG. 20, vessel rod 500 is inserted through aorta 502 of heart 504 via incisions 506 and 508 on opposing walls of aorta 502 such that anvil 510 is centrally positioned within aorta 502.

In FIG. 21, the end of vessel rod 500 is then inserted into the distal end of vein 512 with anvil 510 still centrally positioned within aorta 502. Next, as shown in FIG. 22, vessel rod 500 with accommodated vein 512 is positioned within the corresponding bore 514 in open staple cartridge 516. Rod 500 and vein 512 should be positioned such that a sufficient length of distal end 518 of vein 512 extends beyond the end of cartridge 516 such that distal end 518 can be everted over cylindrical sleeve 520 of cartridge 516 (See FIG. 23). Once vein 512 has been optimally positioned, staple cartridge 516 is clamped around it and secured with clip 522, illustrated in FIG. 24. Now, distal end 518 of vein 512 is everted over sleeve 520 and is securely tied with string 524.

Figure 25:
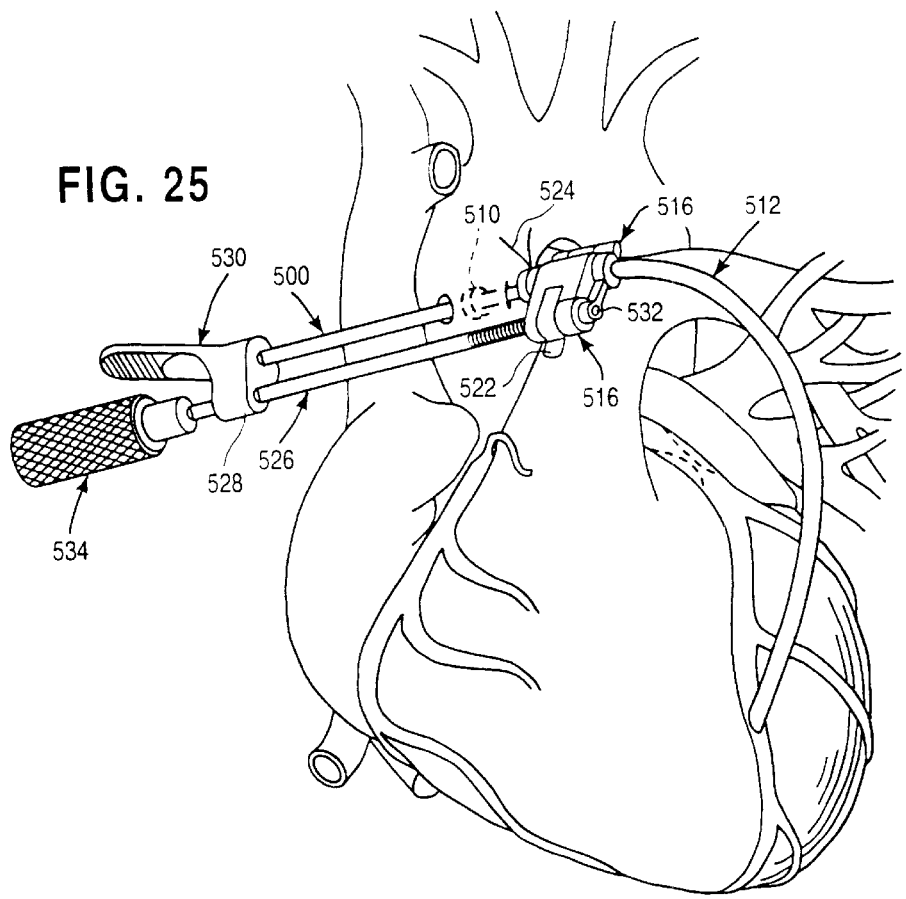
Figure 26:
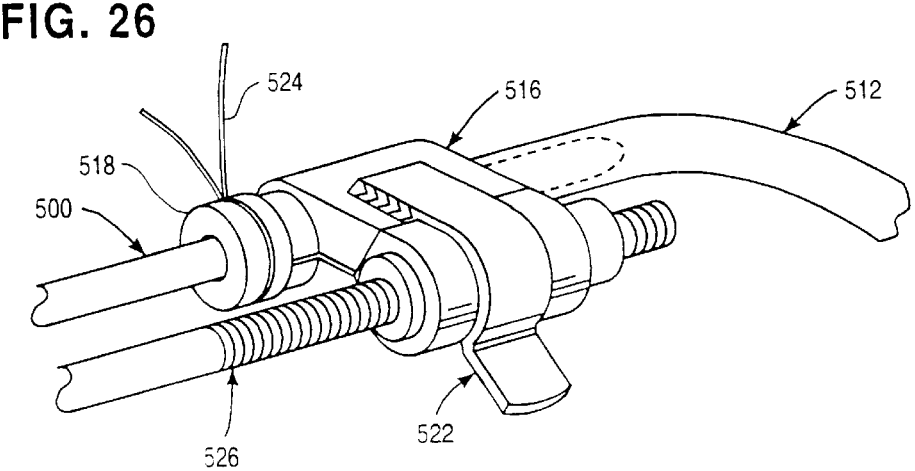

Referring now to FIG. 25, driver rod 526 is slid into bore 528 of handle 530 and then threadedly engaged with bore 532 of staple cartridge 516. FIG. 26 shows a close-up of staple cartridge 516 as it appears in its closed position.

Figure 27:
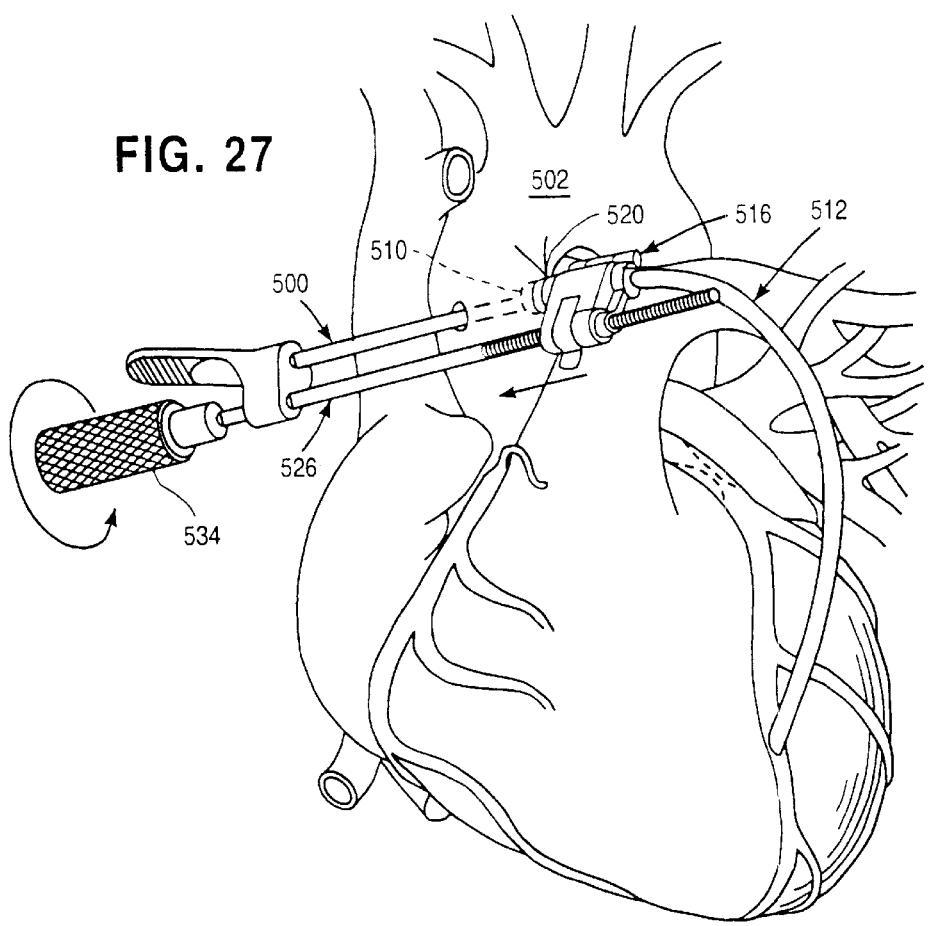
Figure 28:
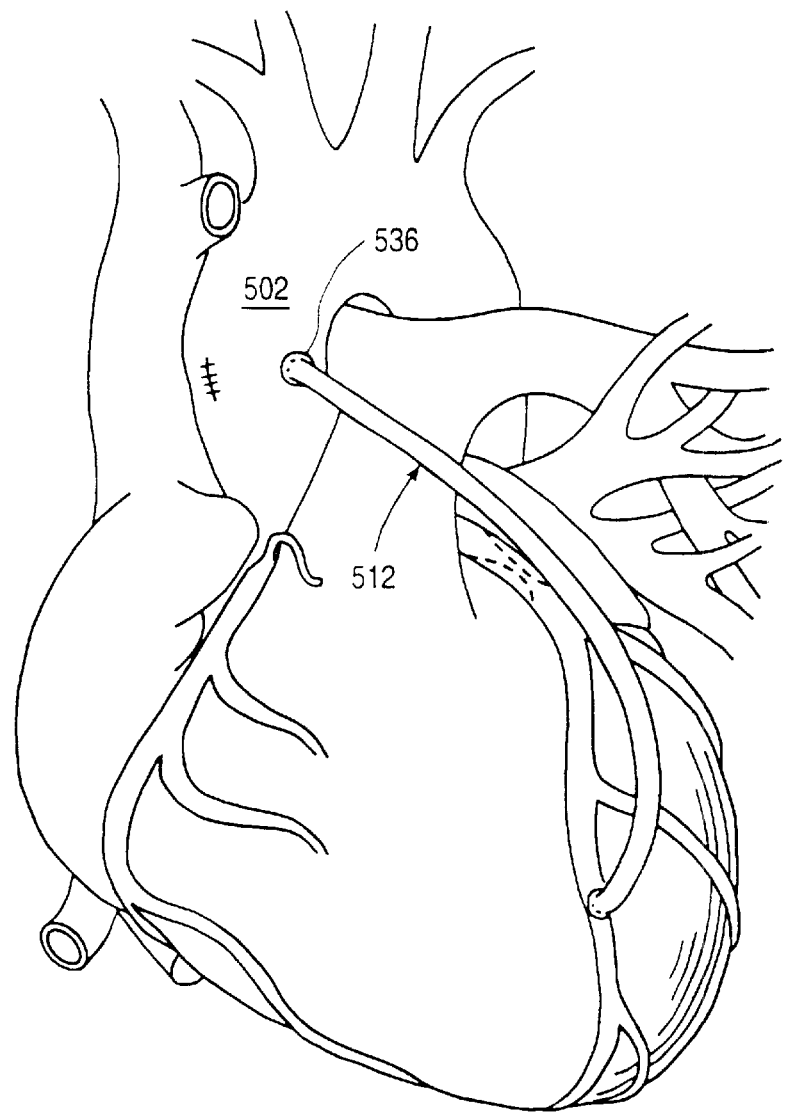

Moving now to FIG. 27, there is shown driver handle 534 rotated in a clockwise direction, bringing together anvil 510 and cylindrical sleeve 520. The clockwise rotation is continued until the aorta wall 502 is engaged with the distal end 518 of vein 512 upon which the staple driver pins (not visible) are fully engaged within each of the corresponding staple shafts (not visible), driving the staples (not visible) through the engaged tissue to create anastomotic bond 536 between aorta 502 and vein 512 (See FIG. 28).

Figure 29:
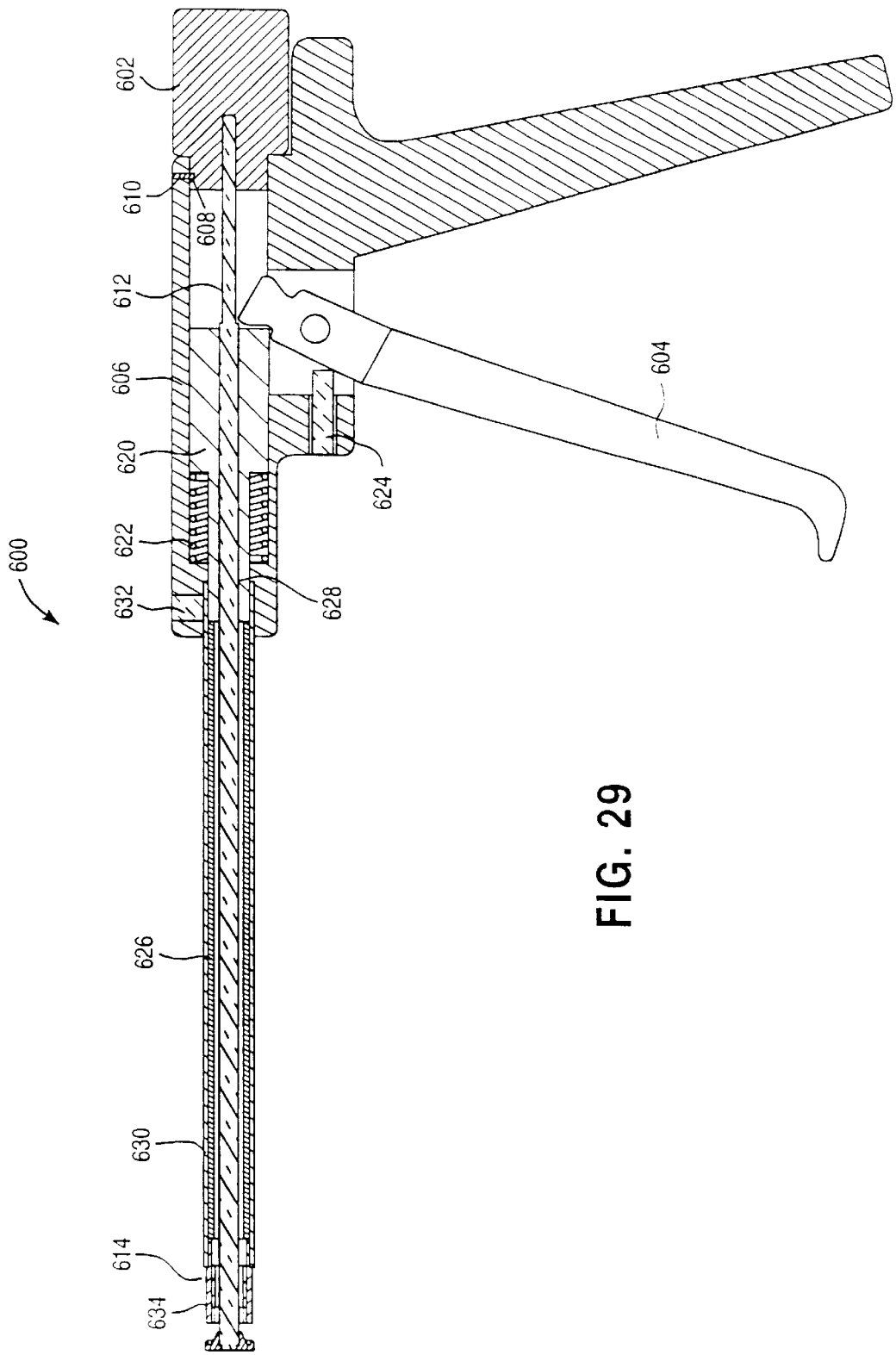
FIG. 29 is a cross-sectional view of another stapler.

Referring to FIG. 29, another stapler 600 is shown. The stapler 600 advantageously provides an actuator 602 for compressing the tissue layers to be stapled and a trigger 604 for firing the staples (not shown). By providing both the actuator 602 and trigger 604, the amount of tissue compression can be controlled independent of staple firing.

The stapler 600 includes a handle 606 with the actuator 602 being rotatably coupled to the proximal end of the handle 606. The actuator 602 has a groove 608 which engages a set screw 610 in the handle 606 so that the actuator 602 can only rotate relative to the handle 606. A rod 612 is threadably coupled to the handle 606 so that rotation of the actuator 602 moves the rod proximally and distally. The rod 612 extends through a housing 614 and an anvil 616 is connected to the distal end of the rod 612. As will be discussed in further detail below, the actuator 602 is rotated to move the anvil 616 relative to a shoulder 618 of the housing 614 for compressing the tissue layers to be stapled.

The trigger 604 is pivotally coupled to the handle 606 and actuation of the trigger 604 fires the staples (not shown) as will be described in further detail below.

The trigger 604 engages a driver 620 which is biased toward the position of FIG. 29 by a spring 622. A stop 624 limits rotation of the trigger 604 beyond the position in FIG. 29. The driver 620 contacts and drives a shaft 626 which extends toward the distal end. The driver 620 preferably has a throughhole 628 having a square cross-sectional shape (not shown) through which the rod 612 extends. The rod 612 has a complementary square cross-sectional shape at a portion extending through the throughhole 628 to prevent rotation of the rod 612. The housing 614 also includes a tube 630 and a guide 634 which has the shoulder 618. The tube is connected to the handle 606 by another set screw 632.

Figure 30:
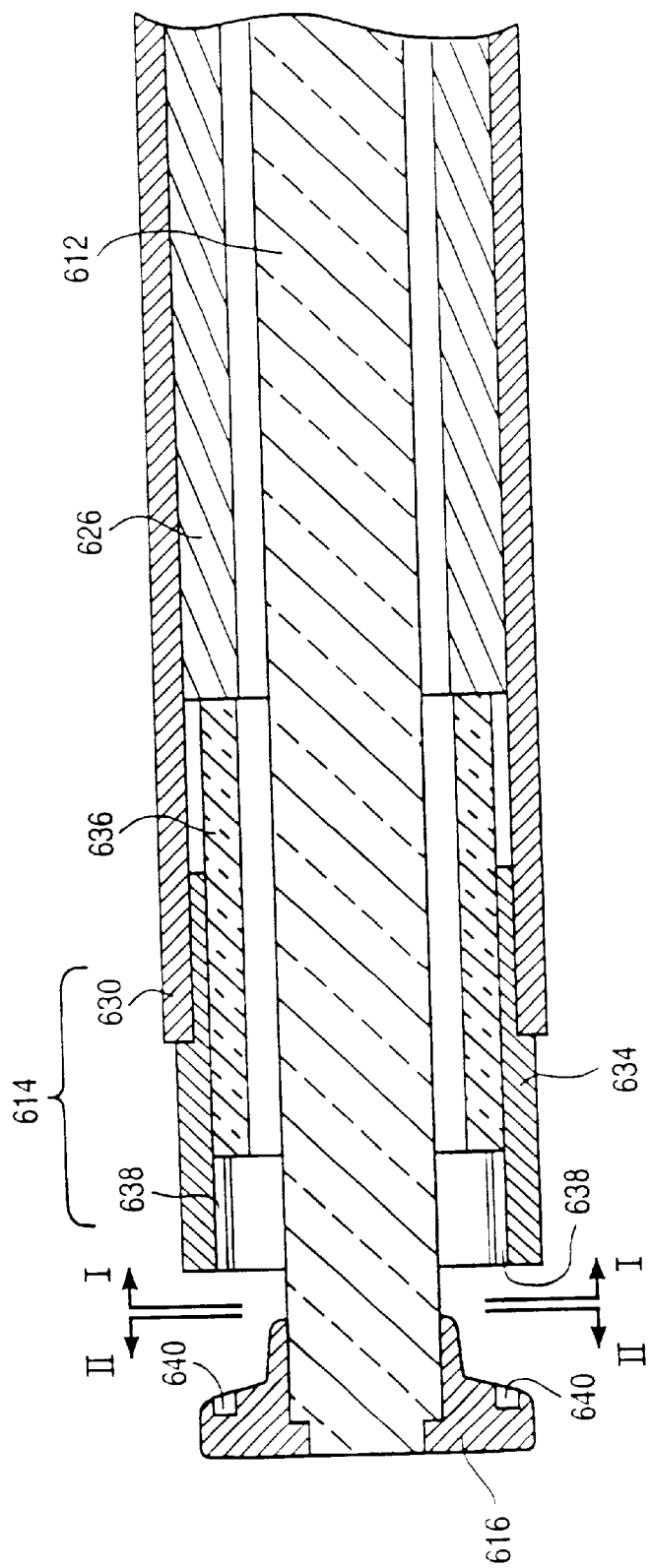
FIG. 30 is a cross-sectional view of a distal end of the stapler of FIG. 30.

Referring to FIG. 30, the distal end of the stapler 600 is shown. The distal end of the shaft 626 engages a staple pusher 636. The staples (not shown) are positioned in cavities 638 and are driven toward recesses 640 in the anvil 616. The staple pusher 636 is slidably coupled to the guide 634 which guides the staple pusher 636 and defines the cavities 638 in which the staples are positioned. The guide 634 is preferably coupled to the tube 630 by a compression fit but may be connected to the tube 630 in any other manner. When the anvil 616 is moved toward the proximal end by rotation of the actuator 602, the tissue layers are compressed between the anvil 616 and the shoulder 618 of the guide 634 as will be described below in connection with FIG. 36.

Figure 31:
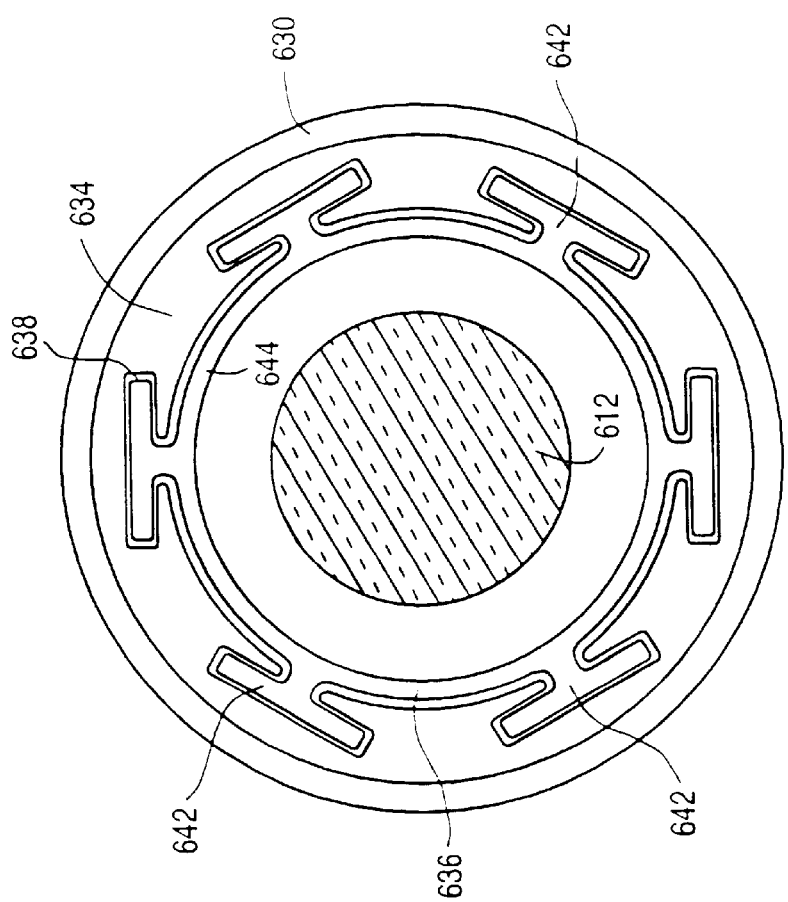
FIG. 31 is a cross-sectional view of FIG. 30 along line I—I.
Figure 32:
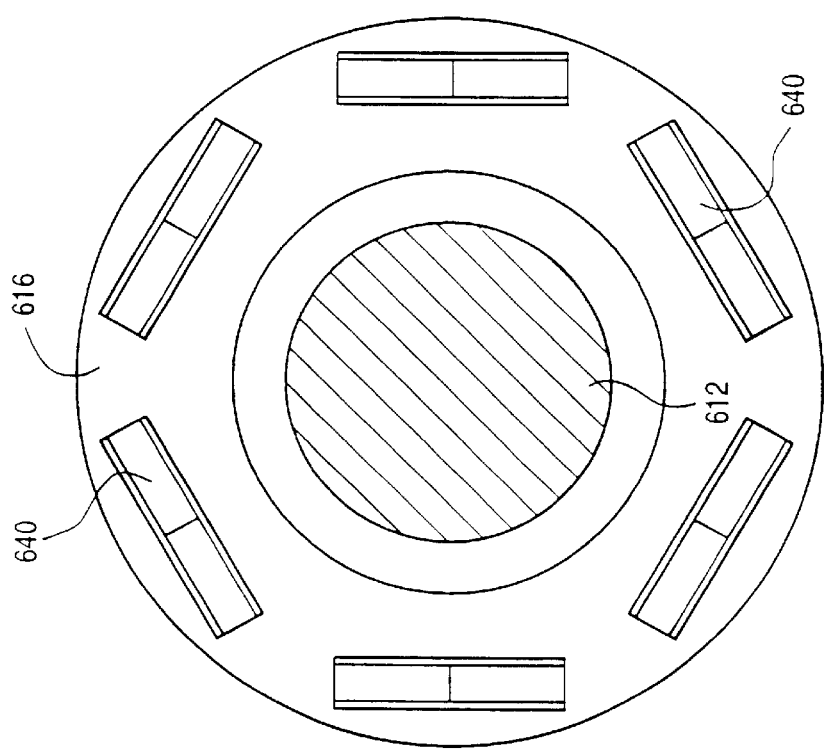
FIG. 32 is a cross-sectional view of FIG. 30 along line II—II.

Referring to FIG. 31, a cross-sectional view of FIG. 30 is shown along line I—I. The guide 634 preferably includes at least five, and more preferably at least six, cavities 638, however, any number of cavities 638 may be provided. The staple pusher 636 includes staple drivers 642 which are positioned in the cavities 638 and extend radially outwardly from a central tube 644. Referring to FIG. 32, another cross-sectional view of FIG. 30 is shown along line II—II. The recesses 640 of the anvil 616 are positioned and shaped to engage and deform the staples being driven from the cavities 638 and have a cross-sectional shape as shown in FIG. 4. The cavities 638 and recesses 640 may have any other configuration, including the tear drop shape of FIGS. 5 and 6, without departing from the scope of the invention.

Figure 34:
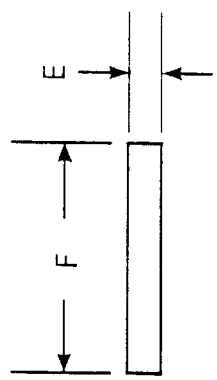
FIG. 34 is a top view of the staple.
Figure 33:
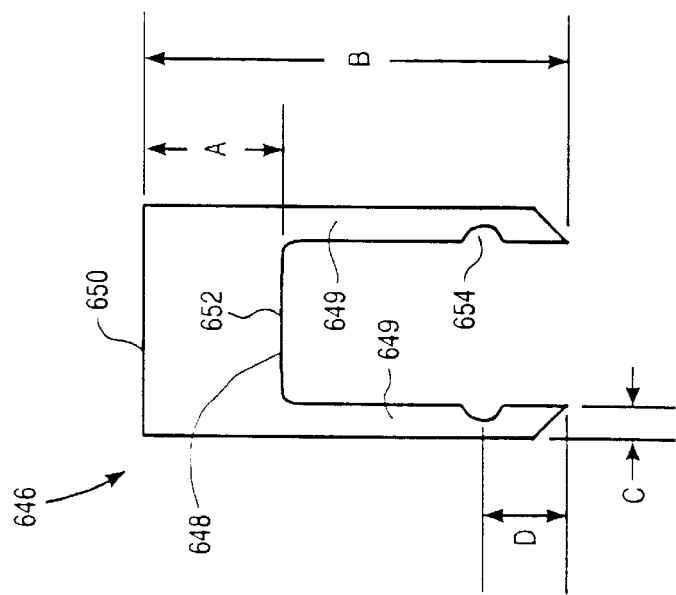
FIG. 33 shows a staple.

Referring to FIGS. 33–34, a preferred staple 646 is shown. The staple 646 includes a tissue compressing portion 648 extending between legs 449 for compressing the tissue layers being stapled. The tissue compressing portion 648 has a height A of preferably 0.040 inches while the overall height B of the staple is preferably 0.125 inches. The height A of the tissue compressing portion is preferably at least 15%, and more preferably at least 25%, and most preferably at least 30% of the overall height B of the staple 646. The tissue compressing portion 648 is preferably solid between a top 650 and bottom 652 of the staple 646 so that the staple 646 is more rigid, however, the tissue compressing portion 648 may also be hollow between the top 650 and bottom 652. The bottom 652 of the tissue compressing portion 648 may also include tissue engaging features, such as atraumatic ridges, for securely grasping the tissue. The tissue compressing portion 648 permits controlled compression of the tissue while the top 650 of the staple 646 is still engaged by the staple pusher 636 for stability.

The staple 646 preferably includes a notch 654 which ensures that the legs 649 bend at the desired location. The legs 649 preferably have a width C of 0.010 inches.

The sharp distal end of each leg is beveled at about 45° and the notch 654 is preferably a distance D of 0.025 inches from the sharp distal end. The notch 654 preferably has a radius of curvature of about 0.005 inches. Referring to FIG. 34, the staple 646 preferably has a thickness E of 0.010 inches and a width F of 0.072 inches. Although the dimensions given above are preferred, the staple 646 may have any other dimensions without departing from the scope of the invention.

Figure 35:
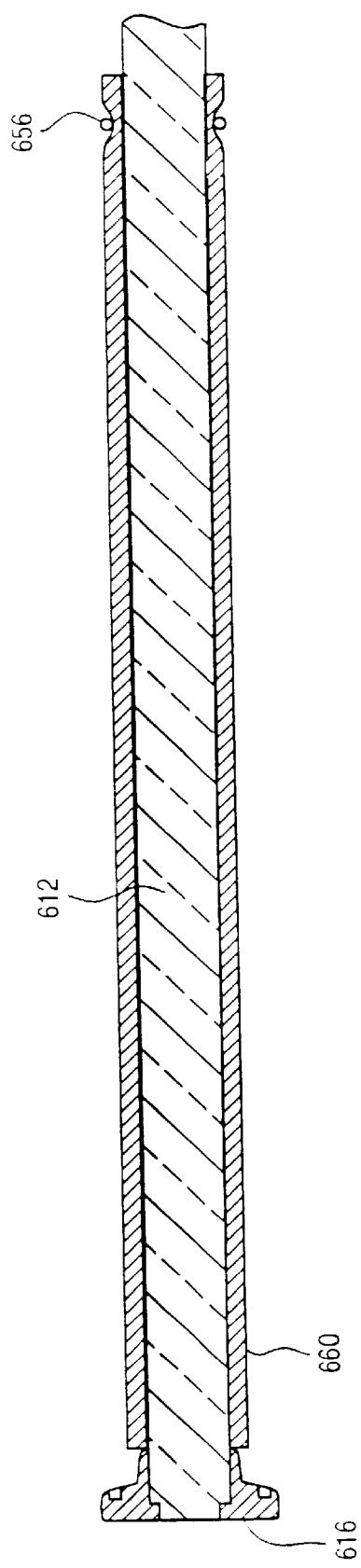
FIG. 35 is a cross-sectional view of a rod having a graft attached thereto.

Operation of the stapler 600 is now described in connection with attaching a graft 660 to a blood vessel such as an aorta or a coronary artery. Referring to FIG. 35, the rod 612 is detached from the stapler 600 by rotating the actuator 602 until the rod 612 is decoupled from the actuator 602. The graft 660, which can be either synthetic or natural, is then fitted over the rod 612 with a suture 656 securing the proximal end of the graft 660 to the rod 612. The rod 612 is then reattached to the actuator 602 so that the graft 660 is positioned almost entirely within the stapler 600.

Figure 36:
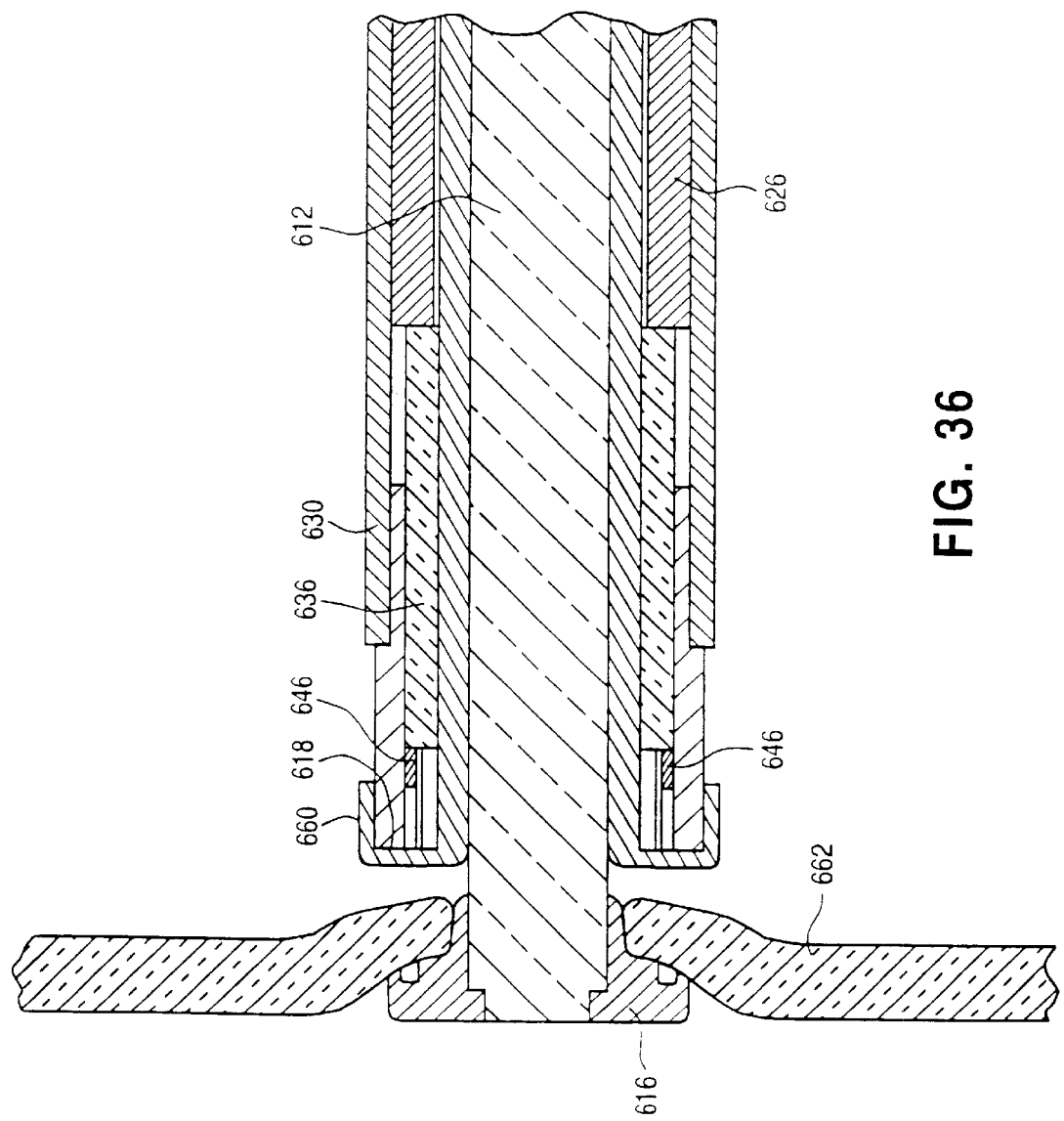
FIG. 36 shows the distal end of the graft everted around the shoulder.
Figure 37:
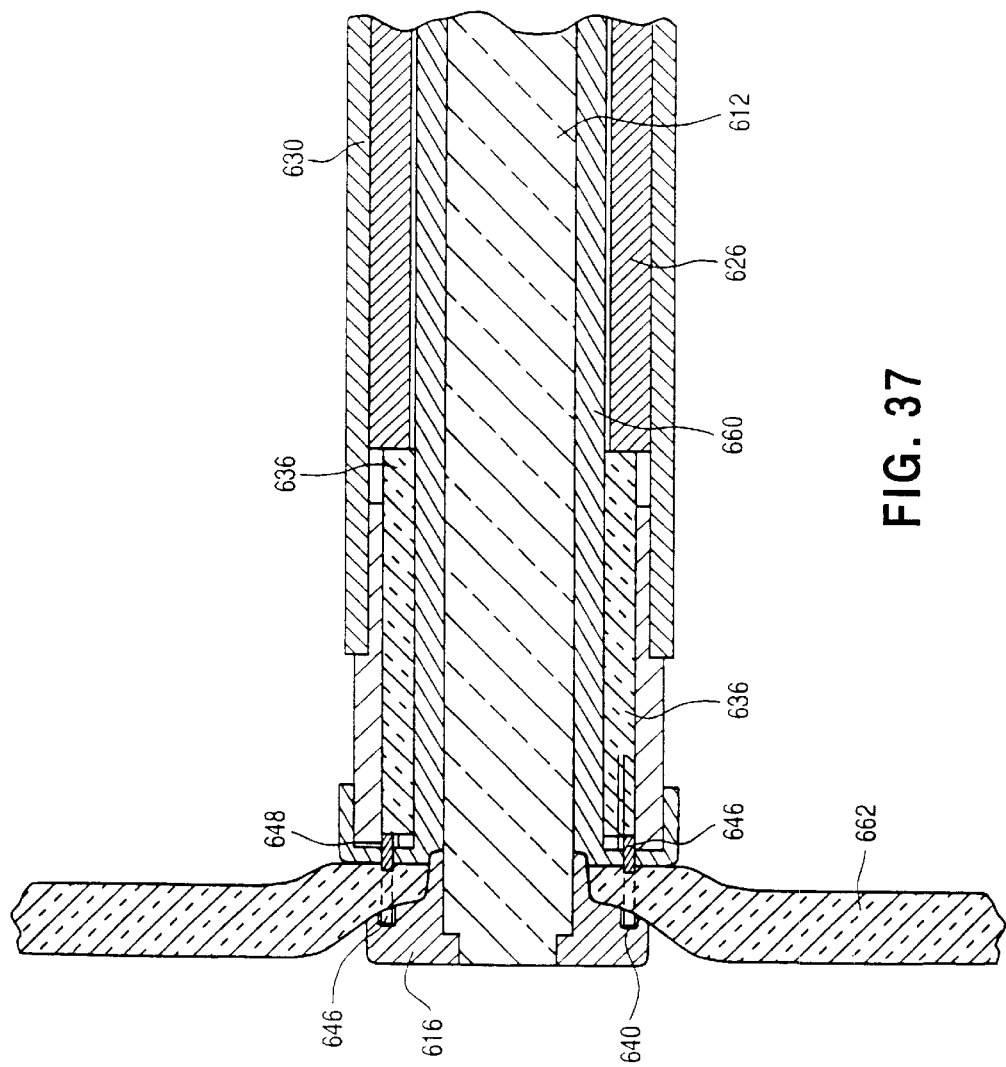
FIG. 37 shows the staples penetrating the graft and engaging an anvil.

Referring to FIG. 36, the distal end of the graft 660 is everted around the shoulder 618. The anvil 616 is then pushed through the opening in the body structure 662, which may be an aorta or a coronary artery, to which the graft 660 is being attached. The actuator 602 is then rotated to compress the body structure 662 and graft 660 between the anvil 616 and shoulder 618 as shown in FIG. 37. An advantage of the stapler 600 is that the compressive force on the graft 660 and body structure 662 may be controlled independent of staple firing. Although it is preferred to movably couple the anvil 616 to the handle 606, the anvil 616 may be fixed to the handle 606 and the shoulder 618 may be movably coupled to the handle 606 for compressing the tissue layers.

Referring still to FIG. 37, the trigger 604 is manipulated to drive the staple pusher 636 and fire the staples 646. The staples 646 are forced against the recesses 640 of the anvil 616 and buckle at the notches 654 (FIG. 34). After the staples 646 have been fired, the actuator 602 is rotated to release compression of the tissue between the anvil 616 and shoulder 618. The anvil 616 and rod 612 are then removed from the graft 660 and the other end of the graft 660 is attached to another body structure, such as an aorta or a coronary artery, thereby completing the graft procedure.

Figure 38:
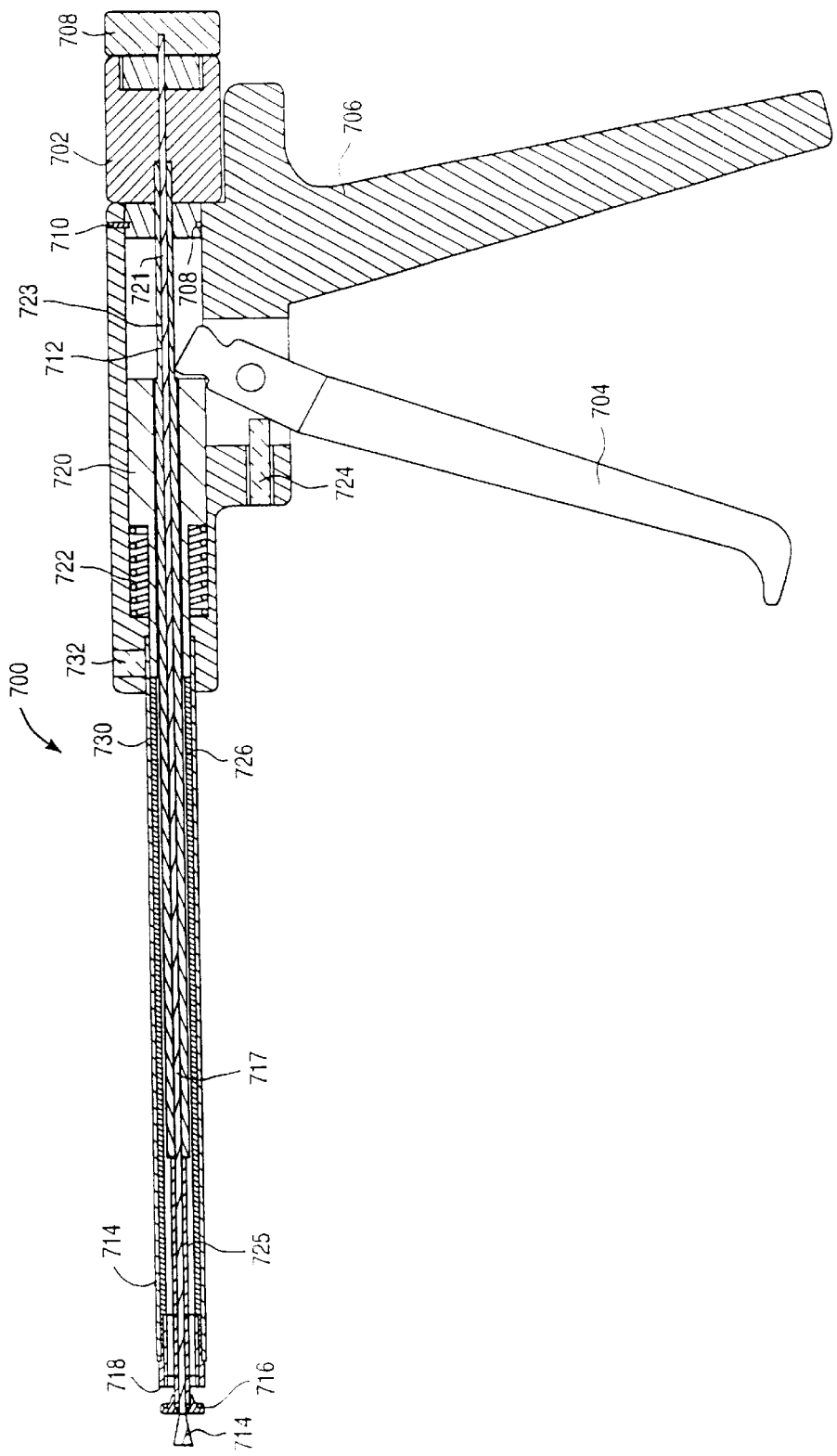
FIG. 38 is a longitudinal cross-sectional vice of yet another stapler.

Referring to FIG. 38, yet another stapler 700 is shown. The stapler 700 includes similar features to the stapler 600 of FIGS. 29–37 and like reference numerals refer to like structure. The stapler 700 includes a handle 706 having an actuator 702 at the proximal end. The actuator 702 has a groove 708 which engages a set screw 710 for rotatably coupling the actuator 702 to the handle 706. A rod 712 is threadably coupled to the handle 706 so that rotation of the actuator 702 moves the rod 612 proximally and distally. An anvil 716 is connected to the distal end of the rod 612. Rotation of the actuator 702 moves the anvil 716 towards and away from a shoulder 718 of a housing 714 to control compression of tissue layers positioned therebetween as discussed above in connection with the stapler 600.

A trigger 704 is pivotally coupled to the handle 706 and actuation of the trigger 704 fires the staples (not shown). The trigger 704 engages a driver 720 which is biased toward the open position of FIG. 40 by a spring 722. A stop 724 limits rotation of the trigger 704 beyond the position in FIG. 40. The driver 720 contacts and drives a shaft 726 which extends toward the distal end. A tube 630 is also connected to the handle 706 by another set screw 732.

Figure 39:
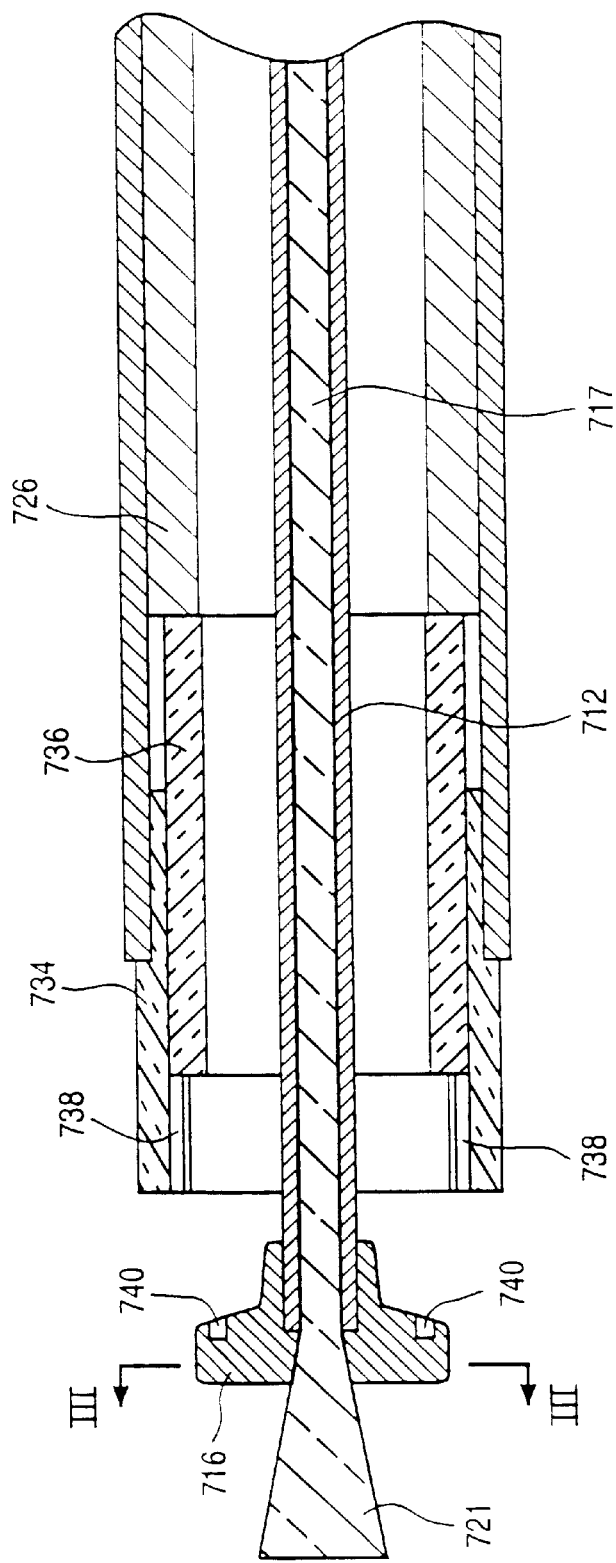
FIG. 39 shows the anvil in a collapsed position.
Figure 40:
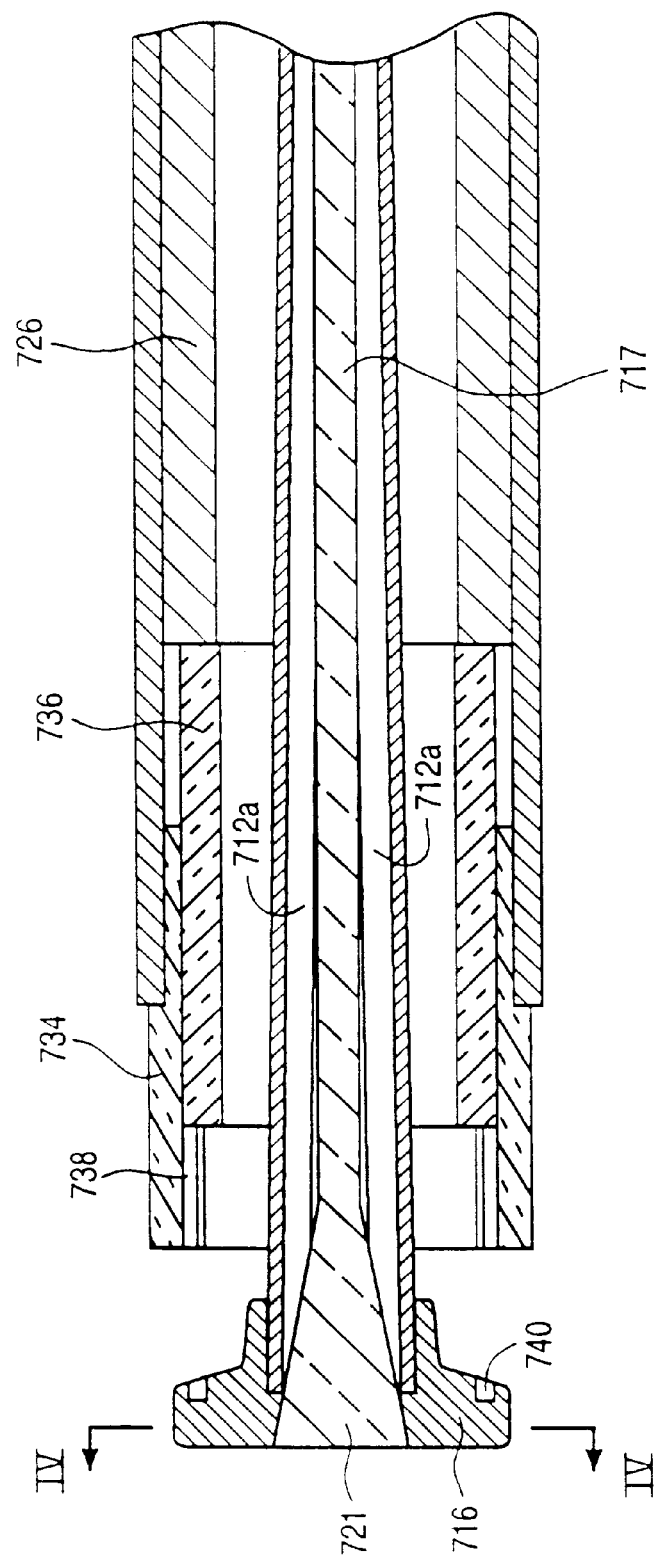
FIG. 40 shows the anvil in an expanded position.

The anvil 716 is expandable from the collapsed position of FIG. 39 to the expanded position of FIG. 40. The anvil 716 is easier to withdraw through the graft after stapling is completed since the anvil 716 can assume the collapsed shape of FIG. 40. The expandable anvil 716 is moved from the collapsed shape to the expanded shape by an expander 717 which extends through the rod 712. The expander 717 is coupled to a knob 719 at the proximal end. The knob 719 is rotatably coupled to the actuator 702 so that rotation of the knob 719 moves the expander 717 distally and proximally. The distal end of the expander 717 has a conical member 721 which engages the anvil 716 to expand the anvil 716 as will be described in greater detail below. The expander 717 preferably has a square cross-sectional shape (not shown) at a portion 721 passing through the distal end of the rod 712 with the distal end of the rod 612 having a complementary shaped square throughhole 723. The square cross-sectional shape of the expander 711 and throughhole 723 prevent rotation of the expander 717 so that rotation of the knob 719 translates into longitudinal motion of the expander 717.

A distal portion 725 of the rod 712 has a reduced diameter so that the rod 712 is more flexible thereby permitting movement from the collapsed position to the expanded position. Referring to FIG. 39, the distal end of the stapler 700 is shown. The distal end of the shaft 726 engages a staple pusher 736. The staples (not shown) are positioned in cavities 738 and are driven toward recesses 740 in the anvil 716. The staple pusher 736 and guide 734 are the same as described above in connection with FIGS. 30–32.

Figure 41:
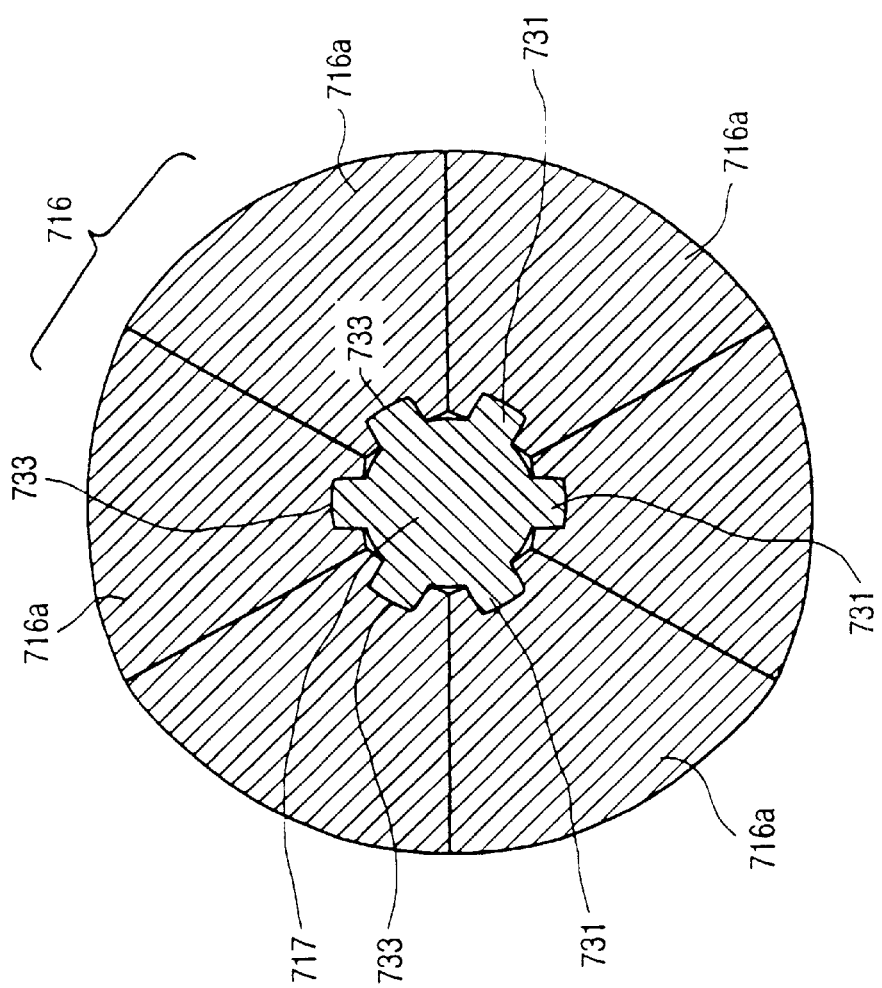
FIG. 41 is a cross-sectional view of FIG. 38 along line III—III.

Referring to FIG. 41, a cross-sectional view of FIG. 38 along line III—III is shown. The expander 717 and anvil 716 are shown with the anvil 716 in the collapsed position. The anvil 716 preferably has at least four, more preferably at least five, and most preferably at least six anvil segments 716A. The rod 712 is split longitudinally along the distal portion 725 (FIG. 38) into six corresponding rod sections 712A (FIG. 40) which each carry one of the anvil segments 716A. FIG. 40 shows two of the rod segments 712A. The rod segments 712A act as springs which permit deflection of the distal portion of the rod 712. The rod segments 712A bias the anvil segments toward the collapsed position of FIG. 39. Referring again to FIG. 41, the expander 717 includes ribs 731 which engage slots 733 in the anvil segments 716A to ensure proper spacing between the anvil segments 716A and prevent displacement of the anvil segments 716A when the staples are fired.

Figure 42:
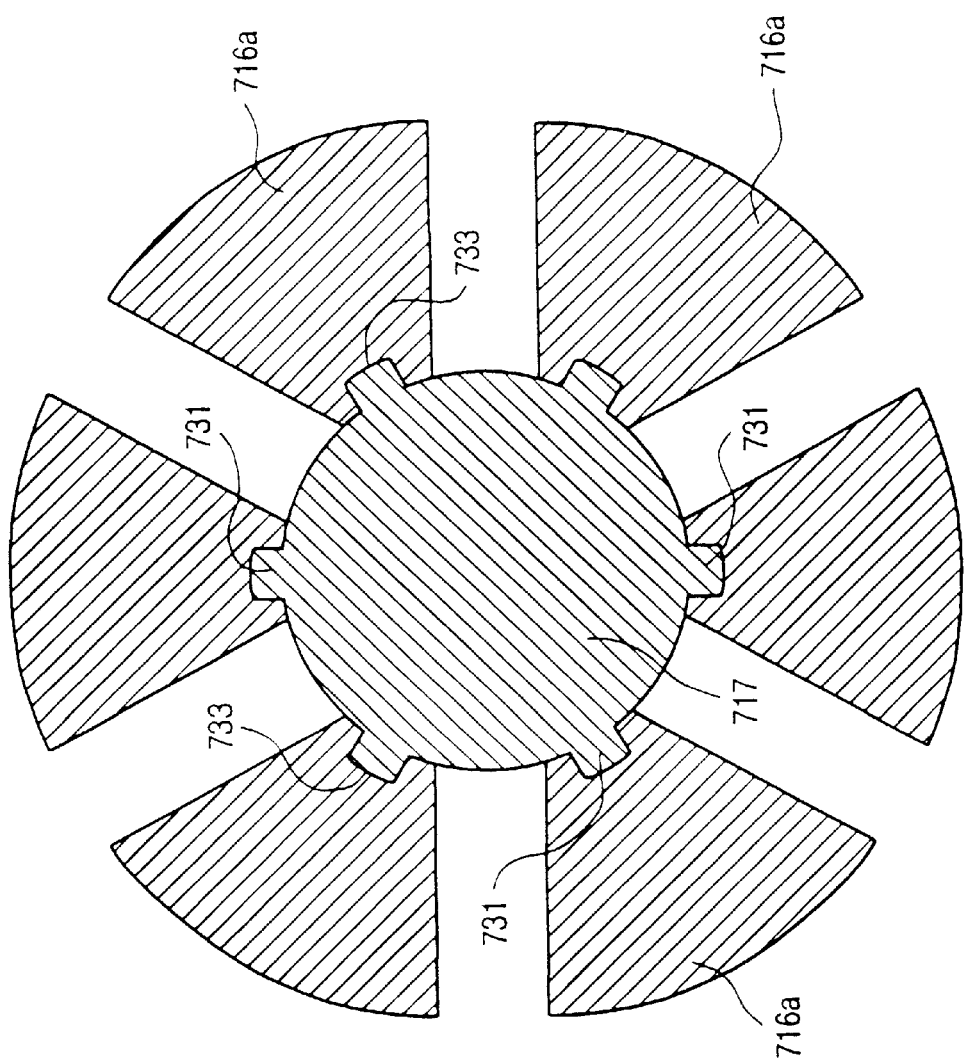
FIG. 42 is a cross-sectional view of FIG. 39 along line IV—IV.

Referring to FIG. 42, a cross-sectional view of FIG. 39 along line IV—IV is shown. The expander 717 is moved toward the proximal end so that the larger diameter portion of the conical member 721 engages the anvil segments 716A and biases the rod segments 712A outwardly as shown in FIG. 39. Each of the anvil segments 716A include one of the recesses 740 shown in FIG. 32 and the recesses 740 are positioned and shaped to engage and deform the staples being driven from the cavities 738 when the anvil 716 is in the expanded position. The anvil segments 716A preferably have a plan area in the collapsed shape which is smaller than the plan area of the recesses when the anvil segments 716A are in the expanded position so that the anvil segments 716A may be easily withdrawn from the stapled area after stapling is completed. The cavities 738 and recesses 740 may be in any other configuration, such as the tear drop shape of FIGS. 5 and 6, without departing from the scope of the invention. The stapler 700 preferably uses the staple 646 described above in connection with FIGS. 34–36, however, any other staple may be used.

Operation of the stapler 700 is now described. The stapler 700 operates in essentially the same as the stapler 600 except for use of the expander 717. The rod 712 is decoupled from the actuator 702 and the expander 717 is decoupled from the knob 719. The rod 712 is then passed through the graft 760 with the anvil 716 in the collapsed shape. The rod 712 and expander 717 are then reattached to the actuator 702 and knob 719. The distal end of the graft 760 is everted around the distal end of the guide 734 and the anvil 716 is pushed through the opening in the body structure to which the graft 760 is being attached. The knob 719 is then rotated so that the expander 717 moves distally and expands the anvil 716 to the expanded position of FIG. 40. Alternatively, the anvil 716 may be positioned in the expanded position before inserting the anvil 716 into the body structure. The actuator 702 is then rotated to compress the body structure and graft between the anvil 716 and shoulder 718. The trigger 704 is then actuated to drive the staple pusher 736 and fire the staples against the anvil segments 716A. After the staples have been fired, the actuator 702 is rotated to release compression of the tissue between the anvil 716 and shoulder 718 and the knob 719 is rotated to move the expander 717 distally thereby causing, the anvil segments 716A to move to the collapsed position. The anvil 716 and rod 712 are then removed from the graft 760 and the other end of the graft 760 is attached to another body structure, such as an aorta or a coronary artery, thereby completing the graft procedure.

It will be understood that the foregoing is only illustrative of the principles of the present invention, and that various modifications can be made by those skilled in the art without departing from the scope and spirit of the invention. For example, the particular stapler structural configurations shown are not critical and other configurations can be used if desired. One possible alternative for the configuration illustrated in FIG. 17 is to have a vessel rod that is retractable (e.g., by means of a telescoping rod). In addition, the vessel rod of this alternative embodiment can be curved to facilitate the anastomotic procedure if necessary. Also, the structure and method of the present invention can be employed thoracoscopically.

What is claimed is:

1. A stapler for connecting a graft to a body structure, comprising:
   a handle;
   an anvil coupled to the handle, the anvil being movable between a collapsed position and
   an expanded position; and
   an expander slidably coupled to the anvil between a first position and a second position, the expander configured to move the anvil from the collapsed position to the expanded position when the expander moves from the first position to the second position.

2. The stapler of claim 1, wherein the anvil comprises a plurality of segments.

3. The stapler of claim 2, wherein each anvil segment has a recess for engaging and deforming a staple.

4. The stapler of claim 2, wherein the plurality of segments are biased toward the collapsed position.

5. The stapler of claim 2, wherein each anvil segment has a slot and the expander comprises a plurality of ribs for engaging each slot.

6. The stapler of claim 1, comprising a rod operably coupled to the handle at a proximal end and connected to the anvil at a distal end.

7. The stapler of claim 6, wherein the rod comprises a plurality of rod segments.

8. The stapler of claim 7, wherein each rod segment is attached to a separate anvil segment.

9. The stapler of claim 1, comprising a staple pusher operably coupled to the handle.

10. The stapler of claim 9, comprising a staple positioned between the staple pusher and the anvil.

11. The stapler of claim 10, comprising a guide having cavities configured to accept at least a portion of each staple therein.

12. The stapler of claim 9, comprising an actuator coupled to the handle, the actuator being configured to drive the staple pusher for driving staples toward the anvil.

13. The stapler of claim 1, wherein the body structure is a blood vessel.

14. The stapler of claim 1, wherein the expander wherein the expander is configured to be moved proximally from the first position to the second position.

15. A stapler for stapling a graft to a body structure, comprising:
   a handle;
   an anvil coupled to the handle, the anvil being movable between a collapsed position and an expanded position; and
   an expander having a proximal portion and a distal end having a greater cross sectional area than the cross sectional area of the proximal portion, the expander operably coupled to the handle and being at least partially disposed within the anvil, the distal end configured to expand the anvil to the expanded position when the distal end is disposed within the anvil.

16. The stapler of claim 15, wherein the expander is slidable within the anvil.

17. A method of connecting a graft to a body structure, comprising the steps of:
   providing a stapler comprising:
      a handle;
      an anvil coupled to the handle, the anvil being movable between a collapsed position and an expanded position; and
      an expander slidably coupled to the anvil between a first position and a second position, the expander configured to move the anvil from the collapsed position to the expanded position when the expander moves from the first position to the second position; and
      a staple pusher operably coupled to the handle; and
   positioning at least one staple between the staple pusher and the anvil;
   inserting the anvil through an opening in a body structure to which the graft is to be stapled;
   expanding the anvil by moving the expander from the first position to the second position;
   moving the staple pusher so that the staple pusher moves a portion of the at least one staple into contact with the anvil.

18. The method of claim 17, wherein the expanding step occurs after the inserting step.

19. The method of claim 17, wherein the providing step further comprises an anvil having a plurality of segments, and wherein the segments move radially.

* * * * *